United States Patent
Lee et al.

(10) Patent No.: US 11,564,908 B2
(45) Date of Patent: Jan. 31, 2023

(54) BETA-LACTAM COMPOUNDS OR SALTS THEREOF FOR USE IN LONG-ACTING PREVENTION OR TREATMENT OF A GLUCOSE METABOLISM DISORDER

(71) Applicant: GLYCOLYSIS BIOMED CO., LTD., Taipei (TW)

(72) Inventors: Feng-Ling Lee, Taipei (TW); Lung-Jr Lin, Taipei (TW); Jyh-Shing Hsu, Taipei (TW); Cheng-Hsien Hsu, Taipei (TW); Yen-Chun Huang, Taipei (TW); Ya-Chien Huang, Taipei (TW); Chun-Tsung Lo, Taipei (TW); Hui-Fang Liao, Taipei (TW); Yu-Wen Liu, Taipei (TW); Yu-Chi Kao, Taipei (TW)

(73) Assignee: GLYCOLYSIS BIOMED CO., LTD., Taipei (TW)

( * ) Notice: Subject to any disclaimer, the term of this patent is extended or adjusted under 35 U.S.C. 154(b) by 20 days.

(21) Appl. No.: 16/747,661

(22) Filed: Jan. 21, 2020

(65) Prior Publication Data
US 2020/0230149 A1 Jul. 23, 2020

Related U.S. Application Data

(60) Provisional application No. 62/795,917, filed on Jan. 23, 2019.

(51) Int. Cl.
| | | |
|---|---|---|
| *A61K 31/43* | (2006.01) | |
| *A61P 3/10* | (2006.01) | |
| *A61K 31/407* | (2006.01) | |
| *A61K 31/4196* | (2006.01) | |
| *A61K 31/426* | (2006.01) | |
| *A61K 31/433* | (2006.01) | |
| *A61K 31/397* | (2006.01) | |

(Continued)

(52) U.S. Cl.
CPC .......... *A61K 31/407* (2013.01); *A61K 31/397* (2013.01); *A61K 31/4196* (2013.01); *A61K 31/426* (2013.01); *A61K 31/43* (2013.01); *A61K 31/431* (2013.01); *A61K 31/433* (2013.01); *A61K 31/545* (2013.01); *A61K 31/546* (2013.01); *A61P 3/10* (2018.01)

(58) Field of Classification Search
CPC .... A61K 31/407; A61K 31/397; A61K 31/43; A61P 3/10
See application file for complete search history.

(56) References Cited

U.S. PATENT DOCUMENTS

2011/0280840 A1* 11/2011 Blaser ..................... A61P 21/00
424/93.4

OTHER PUBLICATIONS

Neu, Harold, Reviews of Infectious Diseases vol. 5, Supplement 2 May-Jun. 1983, pp. 1-20. (Year: 1983).*

(Continued)

*Primary Examiner* — Craig D Ricci
*Assistant Examiner* — Janet L Coppins
(74) *Attorney, Agent, or Firm* — Amin, Turocy & Watson, LLP

(57) ABSTRACT

Provided is a long-acting method for preventing or treating glucose metabolism disorders that includes administering a beta-lactam compound or a pharmaceutically acceptable salt thereof to a subject in need thereof. The method for preventing or treating glucose metabolism disorders has a long-acting effect that lasts more than two days even after medication has been stopped.

4 Claims, 7 Drawing Sheets

(51) Int. Cl.
*A61K 31/431* (2006.01)
*A61K 31/545* (2006.01)
*A61K 31/546* (2006.01)

(56) References Cited

OTHER PUBLICATIONS

Anderson, Chemistry & Biology, vol. 10, 787-797, Sep. 2003. (Year: 2009).*
Thiel Nature Biotechnology vol. 22 No. 5 May 2004, pp. 513-519 (Year: 2004).*
Web printout of https://go.drugbank.com/drugs/DB01053, pp. 1-14, accessed Oct. 6, 2021. (Year: 2021).*
Mahana et al. Genome Medicine 2016, vol. 8 (48), pp. 1-20 (Year: 2016).*

* cited by examiner

BETA-LACTAM COMPOUNDS OR SALTS THEREOF FOR USE IN LONG-ACTING PREVENTION OR TREATMENT OF A GLUCOSE METABOLISM DISORDER

TECHNICAL FIELD

The present disclosure relates to methods for preventing or treating glucose metabolism disorders, and relates particularly to methods for long-acting prevention or treatment of glucose metabolism disorders by administering to a subject in need thereof a beta-lactam compound or a pharmaceutically acceptable salt thereof.

BACKGROUND

Energy is required for normal functioning of body organs. Many tissues utilize fat or protein as an energy source, but others, such as the brain and red blood cells, utilize only glucose. Therefore, glucose is the most important cellular energy source, and thus its metabolism is highly regulated.

A high blood glucose level stimulates secretion of insulin that is produced by pancreatic beta-cells. Insulin secreted into the blood activates the glucose uptake by muscles and adipose cells, leading to the storage of glycogen and triglycerides and to the synthesis of proteins, and thereby the glucose level in the blood is maintained at a proper range. Disruptions of this regulatory network may result in diabetes and its associated syndromes.

Glucose metabolism disorders may lead to hyperglycemia, hyperinsulinemia, or glucose intolerance. An example of a disorder that is often associated with aberrant levels of glucose is insulin resistance, in which liver, adipose, and muscle cells lose their ability to respond to normal blood insulin levels. Obesity and insulin resistance share a complex relationship that leads to the development of various types of metabolic disorder, such as type 2 diabetes. Triglycerides accumulated in adipocytes and free fatty acids released by these cells are both cholesterol precursors that play important roles in the development and progression of diabetes and its associated disorders.

Patients are believed to be prediabetes for a certain period of time before the final clinical diagnosis of diabetes. Impaired fasting glucose (IFG, 100-126 mg/dL) and impaired glucose tolerance (IGT, 140-200 mg/dL) are the two major tests for the diagnosis of prediabetes. The blood glucose levels of people with prediabetes are higher than normal, but are not high enough to be considered as diabetes. Prediabetes carries a higher risk of future diabetes as well as heart diseases. Prediabetes may be controlled by diet and exercise; for example, decreasing body weight by 5 to 10% through diet and exercise may significantly reduce the risk of developing future diabetes. Medical interventions may also be needed to prevent it from becoming diabetes.

To maintain the blood glucose level at a steady level throughout the day, e.g., before and after meals and during the sleep with prolonged fasting hours, medications with different onset, peak and duration of the treatment effects are used. For example, according to the U.S. Food and Drug Administration (FDA), there are four types of insulin treatments, including (i) rapid-acting insulin that starts to function in just 15 minutes after taken and peaks within 30 to 90 minutes while lasting for three to five hours, (ii) short-acting insulin that takes about 30 to 60 minutes to become active and peaks in two to four hours while lasting for five to eight hours, (iii) intermediate-acting insulin that takes one to three hours to start functioning and peaks in eight hours while lasting for 12 to 16 hours, and (iv) long-acting insulin that takes the longest amount of time to start functioning but can last up to 24 hours.

Despite a variety of treatment options, managing glucose metabolism disorders still poses a problem. Patients do not always reach their glycemic targets, and adherence to a treatment plan that relies on frequent and meal-specific dosing leaves room for human error. Treatments with long-acting effects are preferable because the number of injections in the treatment for glucose level control is less, improving the quality of patients' lives and their compliance with the treatment. However, the current longest acting insulin is 42 hours and still requires a daily injection.

Therefore, there is still an unmet need for compositions and methods useful for long-acting therapy of glucose metabolism disorders.

SUMMARY

In view of the foregoing, the present disclosure provides a beta-lactam compound or a pharmaceutically acceptable salt thereof that may prevent or treat a glucose metabolism disorder with a long-acting effect.

In one embodiment of the present disclosure, a method for long-acting prevention or treatment of glucose metabolism disorders in a subject in need thereof is provided. The method comprises administering to the subject an effective amount of the beta-lactam compound or the pharmaceutically acceptable salt thereof.

In one embodiment of the present disclosure, the beta-lactam compound for use in long-acting prevention or treatment of a glucose metabolism disorder is a compound represented by formula (I) or a pharmaceutically acceptable salt thereof:

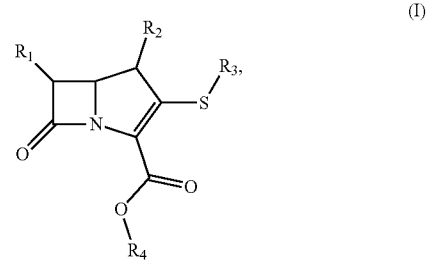

wherein:

$R_1$ and $R_3$ are independently H or a substituted or unsubstituted moiety selected from the group consisting of alkyl, alkenyl, alkynyl, hydroxyalkyl, fluoroalkyl, chloroalkyl, bromoalkyl, iodoalkyl, perfluoroalkyl, aryl, heteroaryl, cycloalkyl, cycloalkenyl, carboxyl, aralkyl, aralkenyl, aralkynyl, heteroaralkyl, heteroaralkenyl, heteroaralkynyl, heterocyclyl, acyl, benzyl, phenyl, aminocarbonyl, aminoalkyl, amino, hydroxyl, alkoxy, acyloxy, silyloxy, amido, imidoyl, carbamoyl, halo, thio, thioether, sulfo, sulfonic, sulfamoyl, thiazolyl, thiazolidinyl, pyrrolyl, pyrrolidinyl, triazolyl, azetidinyl and sulfonamido;

$R_2$ is H or (C1-C6)-alkyl; and $R_4$ is H or (C1-C6)-alkyl or alkali-metal or alkali earth-metal, wherein the alkali-metal or the alkali earth-metal is sodium, potassium, lithium, cesium, rubidium, barium, calcium or magnesium.

In one embodiment of the present disclosure, the compound of formula (I) may be a compound represented by formula (II) below:

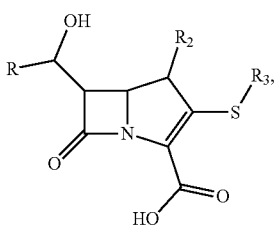
(II)

wherein R is defined as $R_1$ above, and $R_2$ and $R_3$ are as defined above.

In one embodiment of the present disclosure, in the formula (I) or (II), $R_3$ may be represented by one of formulas (I-a) to (I-l) below:

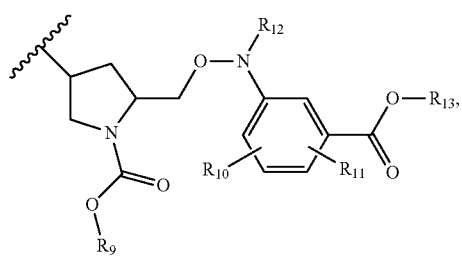
(I-a)

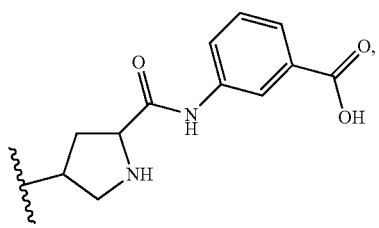
(I-b)

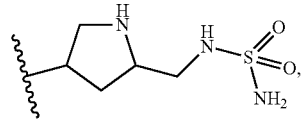
(I-c)

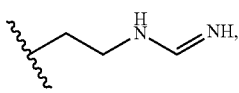
(I-d)

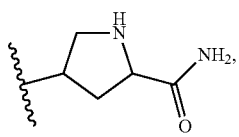
(I-e)

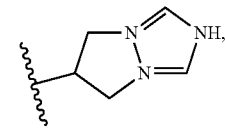
(I-f)

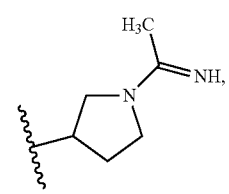
(I-g)

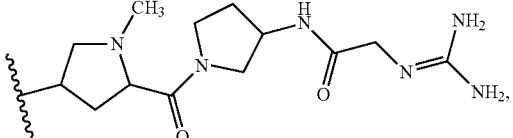
(I-h)

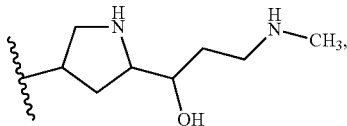
(I-i)

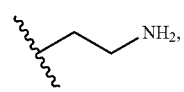
(I-j)

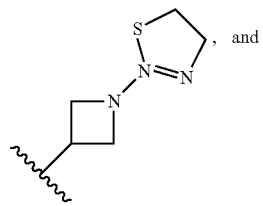
, and
(I-k)

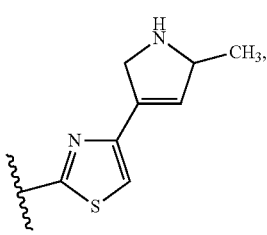
(I-l)

wherein:

$R_9$ and $R_{13}$ are independently H or (C1-C6)-alkyl or alkali-metal or alkali earth-metal, wherein the alkali-metal or the alkali earth-metal is sodium, potassium, lithium, cesium, rubidium, barium, calcium or magnesium;

$R_{10}$ and $R_{11}$ are independently H, halo, cyano, (C1-C6)-alkyl, nitro, hydroxy, carboxy, (C1-C6)-alkoxy, (C1-C6)-alkoxycarbonyl, aminosulphonyl, (C1-C6)-alkylaminosulphonyl, di-(C1-C6)-alkylaminosulphonyl, carbamoyl, (C1-C6)-alkylcarbamoyl, di-(C1-C6)-alkylcarbamoyl, trifluoromethyl, sulphonic acid, amino, (C1-C6)-alkylamino, di-(C1-C6)-alkylamino, (C1-C6)-alkanoylamino, (C1-C6)-alkanoyl(N—(C1-C6)-alkyl)amino, (C1-C6)-alkanesulphonamido, or (C1-C6)-alkyl-S(O)$_n$, wherein n is 0 to 2; and $R_{12}$ is H or (C1-C6)-alkyl.

In one embodiment of the present disclosure, the compound of formula (II) may be a compound represented by following formula:

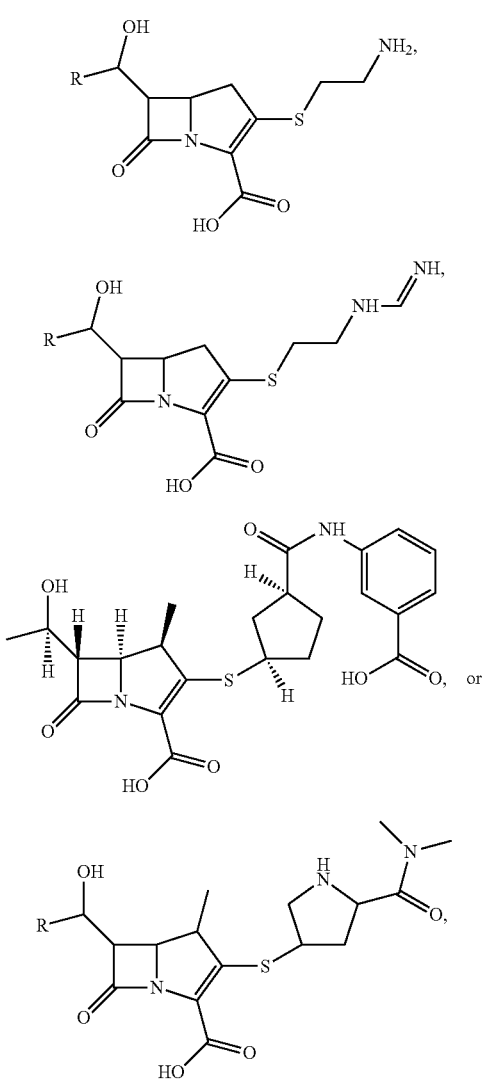

wherein R is defined as $R_1$ above.

In one embodiment of the disclosure, the compound for use in long-acting prevention or treatment of a glucose metabolism disorder is a compound represented by formula (III) or a pharmaceutically acceptable salt thereof:

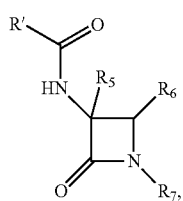

wherein:
R' is H or a substituted or unsubstituted moiety selected from the group consisting of alkyl, alkenyl, alkynyl, hydroxyalkyl, fluoroalkyl, chloroalkyl, bromoalkyl, iodoalkyl, perfluoroalkyl, aryl, phenyl, phenoxyl, benzyl, naphthalenyl, isoxazolyl, piperazinyl, oxopiperazinyl, pyrrolidinyl, pyrazolyl, pyridiazinyl, heteroaryl, pyridinyl, cyclopentapyridinyl, quinolinyl, cycloalkyl, cycloalkenyl, carboxyl, aralkyl, aralkenyl, aralkynyl, heteroaralkyl, heteroaralkenyl, heteroaralkynyl, heterocyclyl, acyl, aminocarbonyl, aminoalkyl, amino, imino, alkylamino, imidazolyl, oxoimidazolidinyl, cyano, furanyl, hydroxyl, alkoxy, acyloxy, silyloxy, amido, imidoyl, carbamoyl, triazinanyl, triazolyl, tetrazolyl, halo, thio, thioether, thienyl, thietanyl, thiophenyl, thiazolyl, thiadiazolyl, sulfo, sulfanyl, sulfonyl, phosphonic, sulfonic and sulfonamido;

$R_5$ is H or a substituted or unsubstituted alkoxy; and $R_6$ is connected with $R_7$ to form a substituted or unsubstituted 5- or 6-membered heterocycle.

In one embodiment of the present disclosure, the compound of formula (III) may be a compound represented by following formula:

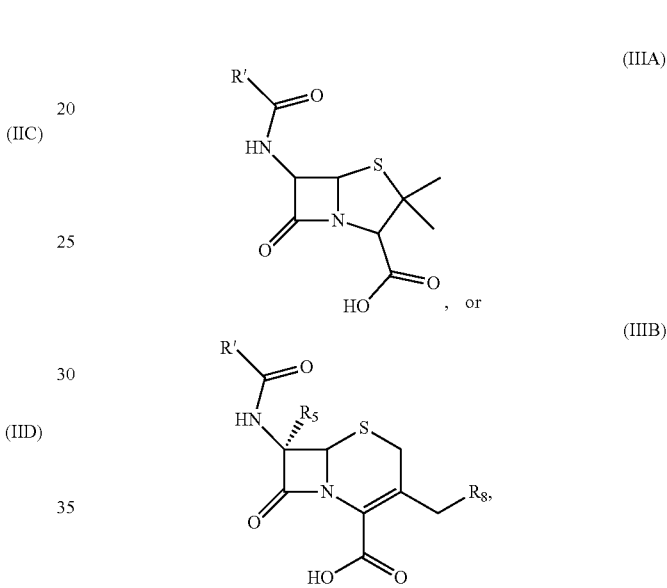

wherein R' and $R_5$ are as defined above, and $R_8$ is defined as R'.

In one embodiment of the present disclosure, in the formula (IIIA), R' is a substituted moiety selected from the group consisting of alkyl, hydroxyalkyl, aryl, heteroaryl, and aralkyl.

In one embodiment of the present disclosure, in the formula (IIIB), $R_5$ is H or methoxy, and $R_8$ is a substituted moiety selected from the group consisting of heteroaryl, heterocyclyl, alkoxy, and thio.

In one embodiment of the present disclosure, the beta-lactam compound for use in long-acting prevention or treatment of a glucose metabolism disorder may be one or more of penicillins, cephalosporins, and carbapenems. In another embodiment, the beta-lactam compound is selected from the group consisting of ertapenem, doripenem, imipenem, meropenem, biapenem, panipenem, tomopenem, lenapenem, tebipenem, razupenem, thienpenem, penicillin G, penicillin O, penicillin N, penicillin K, penicillin V, phenethicillin, propacillin, ampicillin, amoxicillin, azlocillin, carbenicillin, epicillin, methicillin, mezlocillin, oxacillin, piperacillin, cloxacillin, dicloxacillin, flucloxacillin, sulbenicillin, ticarcillin, nafcillin, metampicillin, oxacillin, ceftriaxone, cefalotin, cefoxitin, cefotetan, ceftazidime, cefotaxime, cefepime, cefacetrile, cefadroxil, cefalexin, cefaloglycin, cefalonium, cefaloridine, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefbuperazone, cefminox, cefotiam, cefcapene, cefdaloxime, cefdinir, cefditoren, cefetamet, cefixime, cefmenoxime, cefodizime, cefovecin, cefpimizole, cefpodoxime, cefteram, ceftibuten, ceftiofur, ceftiolene, ceftizoxime, cefoperazone, cefclidine, cefiderocol, cefluprenam, cefoselis, cefozopran, cefpirome, cefquinome, ceftobiprole, ceftaroline, ceftolozane, cefaparole, cefmatilen, cefsumide and a combination thereof.

In one embodiment of the present disclosure, the long-acting prevention or treatment of a glucose metabolism disorder is prevention or treatment of a symptom of the glucose metabolism disorder for more than two days after the administration of the compound (i.e., medication of the compound is stopped). In another embodiment, the long-acting effect on prevention or treatment of the glucose metabolism disorder lasts for at least one week after the administration of the compound. In yet another embodiment, the long-acting effect lasts for at least 6 weeks after the administration of the compound. In still another embodiment, the long-acting effect lasts for 6 to 10 weeks after the administration of the compound.

In one embodiment of the present disclosure, the glucose metabolism disorder is obesity, overweight, hyperglycemia, hyperinsulinemia, glucose intolerance, type 1 diabetes, or type 2 diabetes. In another embodiment, the glucose metabolism disorder is hyperglycemia, and the administration reduces a plasma glucose level in the subject. In yet another embodiment, the glucose metabolism disorder is glucose intolerance, and the administration increases glucose tolerance in the subject.

In one embodiment of the present disclosure, the subject is mammal. In another embodiment, the subject is human.

In one embodiment of the present disclosure, the subject suffers from type 1 diabetes. In another embodiment, the subject suffers from type 2 diabetes.

DETAILED DESCRIPTION

Figure 1:
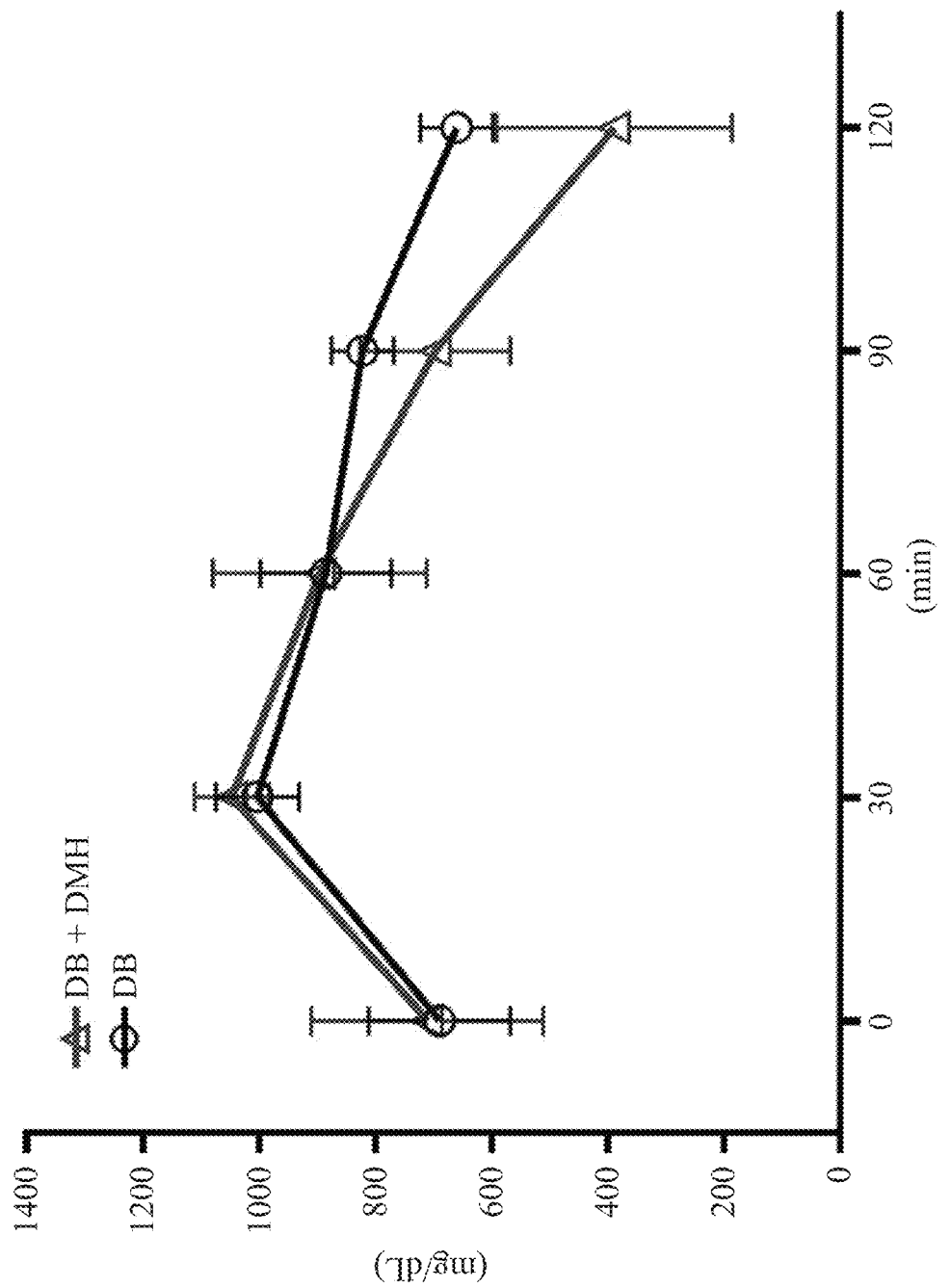
FIG. 1 shows the blood glucose concentrations at week 3 after treatment of ertapenem. DB: db/db mice orally fed with distilled water and intraperitoneally injected (i.p.) with a saline solution. DB+DMH: db/db mice treated with ertapenem (0.41 mg/g bw/day), i.p.

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the following examples for carrying out this disclosure without contravening its spirit and scope, for different aspects and applications.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

The term "patient" or "subject" as used interchangeably herein in the context of therapy refers to a human or a non-human animal, as the recipient of a therapy or preventive care.

The phrase "glucose tolerance" as used herein refers to the ability of a subject to control the level of plasma glucose and/or plasma insulin when glucose intake fluctuates. For example, glucose tolerance encompasses the ability to reduce the level of plasma glucose back to a level before the intake of glucose within about 120 minutes or so.

The phrase "prediabetes" as used herein refers to a condition that may be determined by using either the fasting plasma glucose (FPG) test or the oral glucose tolerance test (OGTT). Both require a person to fast overnight. In the FPG test, a person's blood glucose is measured first in the morning before eating. In the OGTT, a person's blood glucose is checked after fasting and again at 2 hours after drinking a glucose-rich drink. In a healthy individual, a normal test result of FPG would indicate a glucose level of below about 100 mg/dL. A subject with prediabetes would have an FPG level between about 100 mg/dL and about 125 mg/dL. If the blood glucose level rises to about 126 mg/dL or above, the subject is determined to have "diabetes." In the OGTT, the subject's blood glucose is measured after a fast and at 2 hours after drinking a glucose-rich beverage. Normal blood glucose in a healthy individual is below about 140 mg/dL at 2 hours after the drink. In a prediabetes subject, the 2-hour blood glucose is about 140 mg/dL to about 199 mg/dL. If the 2-hour blood glucose rises to 200 mg/dL or above, the subject is determined to have "diabetes."

The present disclosure provides a method to treat a patient suffering from hyperglycemia, hyperinsulinemia, glucose intolerance, etc. Such conditions are also commonly associated with many other glucose metabolism disorders. As such, patients of glucose metabolism disorders can be candidates for therapy according to the methods of the present disclosure.

The phrase "glucose metabolism disorder" encompasses any disorder characterized by a clinical symptom or a combination of clinical symptoms that are associated with an elevated level of glucose and/or an elevated level of insulin in a subject relative to a healthy individual. Elevated levels of glucose and/or insulin may be manifested in the following disorders and/or conditions: type 2 diabetes (e.g., insulin-resistance diabetes), gestational diabetes, insulin resistance, impaired glucose tolerance, hyperinsulinemia, impaired glucose metabolism, prediabetes, metabolic disorders (such as metabolic syndrome which is also referred to as syndrome X), obesity, or obesity-related disorder.

An example of a suitable patient may be one who is hyperglycemic and/or hyperinsulinemic and who is also diagnosed with diabetes mellitus (e.g., type 2 diabetes). "Diabetes" refers to a progressive disease of carbohydrate metabolism involving inadequate production or utilization of insulin and is characterized by hyperglycemia and glycosuria.

The term "hyperglycemia" as used herein is a condition in which an elevated amount of glucose circulates in the blood plasma relative to a healthy individual and can be diagnosed using methods known in the art. For example, hyperglycemia may be diagnosed as having a fasting blood glucose level between 5.6 mM to 7 mM (prediabetes), or greater than 7 mM (diabetes).

The term "hyperinsulinemia" as used herein is a condition in which there are elevated levels of circulating insulin while blood glucose levels may either be elevated or remain normal. Hyperinsulinemia can be caused by insulin resistance which is associated with dyslipidemia such as high triglycerides, high cholesterol, high low density lipoprotein (LDL) and low high density lipoprotein (HDL), high uric acids, polycystic ovary syndrome, type 2 diabetes and obesity. Hyperinsulinemia can be diagnosed as having a plasma insulin level higher than about 2 µU/mL.

A patient having any of the above disorders may be a suitable candidate in need of a therapy in accordance with the present disclosure so as to receive treatment for glucose metabolism disorders. Administering the β-lactam compounds of the present disclosure in such subject may restore glucose homeostasis and may also decrease one or more of symptoms associated with the disorders.

Candidates for treatment using the methods of the present disclosure may be determined using diagnostic methods known in the art, e.g. by assaying plasma glucose and/or insulin levels. Candidates for treatment include those who have exhibited or are exhibiting higher than normal levels of plasma glucose/insulin. Such patients include those who have a fasting blood glucose concentration (where the test is done after 8 to 10 hour fast) of higher than about 100 mg/dL, e.g., higher than about 110 mg/dL, higher than about 120 mg/dL, about 150 mg/dL up to about 200 mg/dL or more. Individuals suitable to be treated also include those who have a 2 hour postprandial blood glucose concentration or a concentration after a glucose tolerance test (e.g., 2 hours after ingestion of a glucose-rich drink), in which the concentration is higher than about 140 mg/dL, e.g., higher than about 150 mg/dL up to 200 mg/dL or more. Glucose concentration may also be presented in the unit of mmol/L, which can be acquired by dividing mg/dL by a factor of 18.

Subjects having, suspected of having, or at the risk of developing a glucose metabolism disorder are contemplated for therapy described herein.

The term "treatment" as used herein refers to a situation that at least an amelioration of the symptoms associated with the condition afflicting the subject is achieved, where amelioration refers to at least a reduction in the magnitude of a parameter, e.g., a symptom, associated with the condition being treated. As such, the treatment includes a situation where the condition, or at least a symptom associated therewith, is reduced or avoided. The treatment includes: (i) as interchangeable with prevention, reducing the risk of development of clinical symptoms, including causing the clinical symptoms not to develop, e.g., preventing disease progression to a harmful or otherwise undesired state; and (ii) inhibition, that is, arresting the development or further development of clinical symptoms, e.g., mitigating or completely inhibiting an active disease (e.g., decreasing the level of insulin and/or glucose in the bloodstream, increasing glucose tolerance to minimize fluctuation of glucose levels, and/or protecting against diseases caused by disruption of glucose homeostasis).

The methods relating to disorders of the glucose metabolism described herein include, for example, use of the β-lactam compounds described above for therapy alone or in combination with other types of therapy. The method involves administering to a subject a β-lactam compound of the present disclosure (e.g., subcutaneously, intramuscularly, or intravenously). As noted above, the methods are useful in the context of treating or preventing a wide variety of disorders related to glucose metabolism.

The methods of the present disclosure involve administering a β-lactam compound of the present disclosure in a subject who has a glucose metabolism disorder. The methods of the present disclosure include administering a compound represented by formula (I), (II), or (III) as disclosed above in the context of a variety of conditions including the disorders as exemplified above (in both prevention and post-diagnosis therapy).

In one embodiment, the β-lactam compound of the present disclosure for use in long-acting prevention or treatment of a glucose metabolism disorder may be carbapenems represented by formula (IIA), (IIB), (IIC), or (IID), such as ertapenem, doripenem, imipenem, meropenem, biapenem, and panipenem.

In one embodiment, the β-lactam compound of the present disclosure for use in long-acting prevention or treatment of a glucose metabolism disorder may be penicillins represented by formula (IIIA), such as penicillin G, penicillin O, penicillin N, penicillin K, penicillin V, phenethicillin, propacillin, ampicillin, amoxicillin, azlocillin, carbenicillin, epicillin, methicillin, mezlocillin, oxacillin, piperacillin, cloxacillin, dicloxacillin, flucloxacillin, sulbenicillin, ticarcillin, nafcillin, metampicillin, and oxacillin.

In one embodiment, the β-lactam compound of the present disclosure for use in long-acting prevention or treatment of a glucose metabolism disorder may be cephalosporins represented by formula (IIIB), such as ceftriaxone, cefalotin, cefoxitin, cefotetan, ceftazidime, cefotaxime, cefepime, cefacetrile, cefadroxil, cefalexin, cefaloglycin, cefalonium, cefaloridine, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefbuperazone, cefminox, cefotiam, cefcapene, cefdaloxime, cefdinir, cefditoren, cefetamet, cefixime, cefmenoxime, cefodizime, cefovecin, cefpimizole, cefpodoxime, cefteram, ceftibuten, ceftiofur, ceftiolene, ceftizoxime, cefoperazone, cefclidine, cefiderocol, cefluprenam, cefoselis, cefozopran, cefpirome, cefquinome, ceftobiprole, ceftaroline, ceftolozane, cefaparole, cefmatilen, and cefsumide.

In the methods of the present disclosure, the β-lactam compound may be administered in a form of a pharmaceutical composition. The pharmaceutical composition may comprise one or more of the β-lactam compounds described herein and/or an additional therapeutic agent for the disorder as exemplified above. The pharmaceutical composition may be administered to a subject (e.g., a human patient) to, for example, achieve and/or maintain glucose homeostasis, e.g., to reduce a glucose level in the bloodstream and/or to reduce an insulin level to a range found in a healthy individual. Subjects for treatment include those having a glucose metabolism disorder as described herein.

In one embodiment, the pharmaceutical compositions of the present disclosure further comprise a pharmaceutically acceptable carrier, diluent, excipient, or solvate, and may be prepared in suitable dosage forms. Examples of suitable dosage forms are tablets, capsules, coated tablets, granules, solutions and syrups for oral administration; medicated plasters, pastes, creams and ointments for transdermal administration; suppositories for rectal administration; and sterile solutions for administration via the injection or aerosol route.

Other examples of suitable dosage forms are those with sustained release and based on, e.g., liposomes, for administration via either the oral or injection route.

The dosage forms may also contain other conventional ingredients, for instance, a preserving agent, a stabilizer, a surfactant, a buffer, an osmotic pressure-regulating salt, an emulsifier, a sweetener, a colorant, a flavoring agent and the like.

In addition, when required for particular therapies, the pharmaceutical composition according to the present disclosure may also contain other pharmacologically active ingredients whose simultaneous administration is useful.

The amount of the beta-lactam compound according to the present disclosure may vary within a wide range based on, for instance, the type of disease to be treated, the severity of the disease, the body weight of the patient, the dosage form, the selected route of administration, the number of daily administrations, and the efficacy of the selected beta-lactam compound. However, a person skilled in the art may determine the optimum amount in a simple and routine manner based on the present disclosure as needed.

In the methods of the present disclosure, a therapeutically effective amount of the beta-lactam compound is administered to a subject in need thereof. That is to say, the beta-lactam compound causes the level of plasma glucose and/or insulin to return to a normal level relative to a healthy individual when the compound is delivered to the bloodstream in an effective amount to a patient who previously did not have a normal level of glucose/insulin relative to a healthy individual prior to being treated. The amount administered varies depending upon the goal of the administration, the health and physical condition and age of the individual to be treated, the activity of the compounds employed, the treating clinician's assessment of the medical situation, the condition of the subject, the body weight of the subject, the severity of the dysregulation of glucose/insulin and the stage of the disease, and other relevant factors. The size of the dose will also be determined by the existence, nature, and extent of any adverse side-effects that might accompany the administration of the compound.

It is expected that the amount will fall in a relatively broad range that may be determined through routine trials. For example, the amount of the compound employed to restore glucose homeostasis is not more than about the amount that could otherwise be irreversibly toxic to the subject (i.e., the maximum tolerated dose). In other cases, the amount is around or even well below the toxic threshold, but still in an effective concentration range, or even as low as the threshold dose.

Also, suitable doses and dosage regimens may be determined by comparisons to indicators of glucose metabolism. Such dosages include dosages which result in the stabilized levels of glucose and insulin, for example, comparable to a healthy individual, without significant side effects. Dosage treatment may be a single dose schedule or a multiple dose schedule (e.g., including ramp and maintenance doses). As indicated below, a pharmaceutical composition may be administered in conjunction with other agents, and thus doses and regiments may vary in this context as well to suit the needs of the subject.

Individual doses are typically not less than an amount required to produce a measurable effect on the subject, and may be determined based on the pharmacokinetics and pharmacology for absorption, distribution, metabolism, and excretion ("ADME") of the compounds or their by-products, and thus based on the disposition of the composition within the subject. This includes consideration of the route of administration as well as dosage amount, which may be adjusted for enteral (applied via the digestive tract for systemic or local effects when retained in part of the digestive tract) or parenteral (applied by routes other than the digestive tract for systemic or local effects) applications. For instance, administration of the compounds is typically via injection and often intravenous, intramuscular, or a combination thereof.

The phrase "in an effective amount" means that there is a detectable difference between a level of an indicator measured before and after administration of the amount of a particular therapy. Indicators include but are not limited to glucose and insulin. For example, it may mean that the administration of that amount to an individual, either in a single dose, as part of a series of the same or different compositions, is effective to help restore homeostasis of glucose metabolism as assessed by glucose and/or insulin levels in a subject. As noted above, the therapeutically effective amount may be adjusted in connection with dosing regimen and diagnostic analysis of the subject's condition (e.g., monitoring for the levels of glucose and/or insulin in the plasma) and the like.

The dosage forms of the pharmaceutical composition according to the present disclosure may be prepared according to techniques that are well known to pharmaceutical chemists, including mixing, granulation, compression, dissolution, sterilization and the like.

The term "long-acting" or "long-acting effect" as used interchangeably herein as an effect on preventing or treating a glucose metabolism disorder lasting for at least 24 hours, at least 48 hours, at least 72 hours, at least 96 hours, at least one week, at least two weeks, at least three weeks, at least four weeks, at least five weeks, at least six weeks, at least seven weeks, at least eight weeks, at least nine weeks, at least ten weeks, at least eleven weeks, or at least twelve weeks even after the medication of the β-lactam compound is stopped to be administered. In one embodiment, the β-lactam compounds of the present disclosure are not only useful for preventing or treating a glucose metabolism disorder, but also exhibit a long-acting effect on preventing or treating a glucose metabolism disorder even after administering to the subject in need thereof, wherein the long-acting effect may last for at least two days, at least one week, at least two weeks, at least three weeks, at least four weeks, at least five weeks, at least six weeks, at least seven weeks, at least eight weeks, at least nine weeks, at least ten weeks, at least eleven weeks or at least twelve weeks.

EXAMPLES

The following examples are put forth so as to provide those of ordinary skill in the art with a complete disclosure and description of how to make and use the present disclosure, and are not intended to limit the scope of what to be regarded as the invention nor to represent that the experiments below are all or the only experiments performed. Efforts have been made to ensure accuracy with respect to numbers used (e.g., amounts, weights, temperature, etc.) but some experimental errors and deviations should be accounted for.

Materials and Methods

The materials and methods used in the following examples were described in detail below. The materials used in the present disclosure but unannotated herein are commercially available.

(1) Animals

In the following examples, leptin receptor gene (Lepr) defective db/db mice that exhibit insulin resistance similar to patients with type 2 diabetes are used to investigate the effects of candidate compounds in the regulation of blood glucose homeostasis.

Four to five weeks old db/db mice (BKS.Cg-Dock7$^m$+/+ Lepr$^{db}$/JNarl) and m/m mice (BKS.Cg-Dock7$^m$+/Dock7$^m$+) were obtained from National Laboratory Animal Center (Nangang, Taipei, Taiwan). These animals were maintained in a facility with a 12-h dark-light cycle at 24±2° C. and 65±5% humidity and were provided food (No. 5001; PMI Nutrition International, Brentwood, Mo.) and water ad libitum. For experiments, the average body weight of m/m mice was approximately 20 g, and that of db/db mice was approximately 30 g.

The mouse body weight (bw) and the amounts of water and food intake were recorded weekly for the entire study period.

(2) Fasting Plasma Glucose (FPG) Measurement

For each mouse, blood was sampled from the tail vein and measured for FPG levels using a blood glucose meter (OneTouch UltraEasy, Johnson & Johnson, USA) at a pre-destined time point.

(3) Oral Glucose Tolerance Test (OGTT)

For OGTT, all mice were fasted for 16 hours before test, but water was provided ad libitum. Blood was sampled from the tail vein, and FPG levels were measured and recorded as the basic blood glucose levels. After FPG measurements, mice were orally given with 2 mg/g of glucose (a 20% glucose solution) and measured for blood glucose levels at 15, 30, 60, and 120 mins after feeding. The total area under the curve (AUC) in OGTT was plotted and calculated by the Area Under Coordinates Program (StatsToDo Server, Department of Obstetrics and Gynecology, Chinese University of Hong Kong).

(4) Other Analyses

Inflammatory markers such as serum aspartate aminotransferase (AST), alanine aminotransferase (ALT), blood urea nitrogen (BUN), creatinine (Cr), and hemoglobin A1c (HbA1c) were measured using a BMC-Hitachi 717 chemistry auto analyzer.

For histopathological assessment, all mice were sacrificed by 95% $CO_2$ asphyxiation at the end of the study period. Their brain, liver, kidney, pancreas, and epididymal fat pads were removed, fixed in 10% phosphate-buffered formalin, and embedded in paraffin. Tissues embedded in paraffin were cut into 4-μm-thick sections that were then stained with hematoxylin-eosin (i.e., H&E stain).

(5) Statistical Analysis

Results calculated from at least 6 mice in each experimental group were shown as means±SEM. A P value <0.05 was considered significant (ANOVA followed by Duncan's test). Medical treatments were considered effective (P value <0.05) in decreasing blood glucose levels if the FPG levels after treatment were significantly lower than those before treatment, or if the values of oral glucose tolerance (OGT) after treatment were significantly higher than those before treatment.

Example 1: Effect of Ertapenem Treatment on a Glucose Metabolism Disorder

In this example, the effect of ertapenem (hereinafter also abbreviated as "DMH") on a glucose metabolism disorder is investigated in comparison with metformin (Met), a known first line pharmacotherapy for treating type 2 diabetes.

Twelve 7- or 8-week-old db/db mice were randomly divided into 2 groups, and intraperitoneally injected (i.p.) with or without ertapenem (i.e., the DB+DMH or DB groups, respectively). The treatments of each group were specifically explained in Table 1 below.

TABLE 1

Mice were divided into 2 groups for different treatments

| Group | Mice Used | Treatment |
|---|---|---|
| DB | 6 m/m mice | Saline, i.p. (10 μL/g body weight (bw)/day) |
| DB + DMH | 6 db/db mice | Ertapenem, i.p. (0.41 mg/g bw/day) |

Each mouse was treated with saline or ertapenem intraperitoneally once a day, and such the treatments lasted for a total three weeks. The tests and results were described as follows.

(1-1) Ertapenem Treatment Reduced the Food and Water Intake

As shown in Table 2 below, it was found that the mice treated with ertapenem (i.e., the DB+DMH group) had the reduced food and water intake during the entire study period (P<0.05). This result clearly showed that ertapenem is effective in controlling the food and water intake of diabetes mice.

TABLE 2

Average food and water intake among mouse groups

| | Week | |
|---|---|---|
| Groups | Diet intake (g/mice/day) | Water intake (mL/mice/day) |
| DB | 5.8 ± 1 | 13.3 ± 2.7 |
| DB + DMH | 5.0 ± 0.9* | 6.8 ± 1.6* |

*P < 0.05

(1-2) Ertapenem Treatment Increased Oral Glucose Tolerance

OGTT was performed at week 3, i.e., the end of the ertapenem treatment. As shown in FIG. 1, the glucose concentration in the DB+DMH group was significantly lower than that in the DB group at time points of 90 min and 120 min.

Further, the total area under the curve (AUC) in OGTT was plotted and calculated as shown in Table 3. Results showed that the AUC of ertapenem-treated mice (DB+DMH group) was significantly smaller (P<0.05) than that of untreated mice (DB group).

TABLE 3

OGTT AUCs of two mouse groups

| Groups | Week 3 Weeks |
|---|---|
| DB | 1666 ± 81 |
| DB + DMH | 1298 ± 186* |

*P < 0.05

(1-3) Plasma Biochemical Parameter Analysis

AST and ALT, formerly called as serum glutamic oxaloacetic transaminase (GOT) and serum glutamic pyruvic transaminase (GPT), respectively, are inflammatory markers of the liver. BUN and Cr are inflammatory markers of the kidney. These markers and HbA1c were measured at week 3, i.e., the end of the ertapenem treatment. The results were reported in Table 4. It was found that the levels of AST, ALT, BUN, and HbA1c in the diabetes mice were significantly reduced by treating with ertapenem.

TABLE 4

Plasma biochemical parameters in mice of two mouse groups

| | Week | | | | |
|---|---|---|---|---|---|
| Groups | AST (U/L) | ALT (U/L) | BUN (mg/dL) | Creatinine (mg/dL) | HbA1c (%) |
| DB | 99 ± 21 | 71 ± 14 | 36 ± 3 | 0.54 ± 0.02 | 7.6 ± 0.5 |
| DB + DMH | 61 ± 7* | 34 ± 6* | 27 ± 2* | 0.57 ± 0.02* | 6.1 ± 0.8* |

*P < 0.05

(1-4) Histological Change of Ertapenem Treatment

At the end of the study period, all mice were sacrificed and their brains, livers, kidneys, pancreases, and epididymal fat pads (EFP) were collected and examined histologically for injuries.

Figure 2:
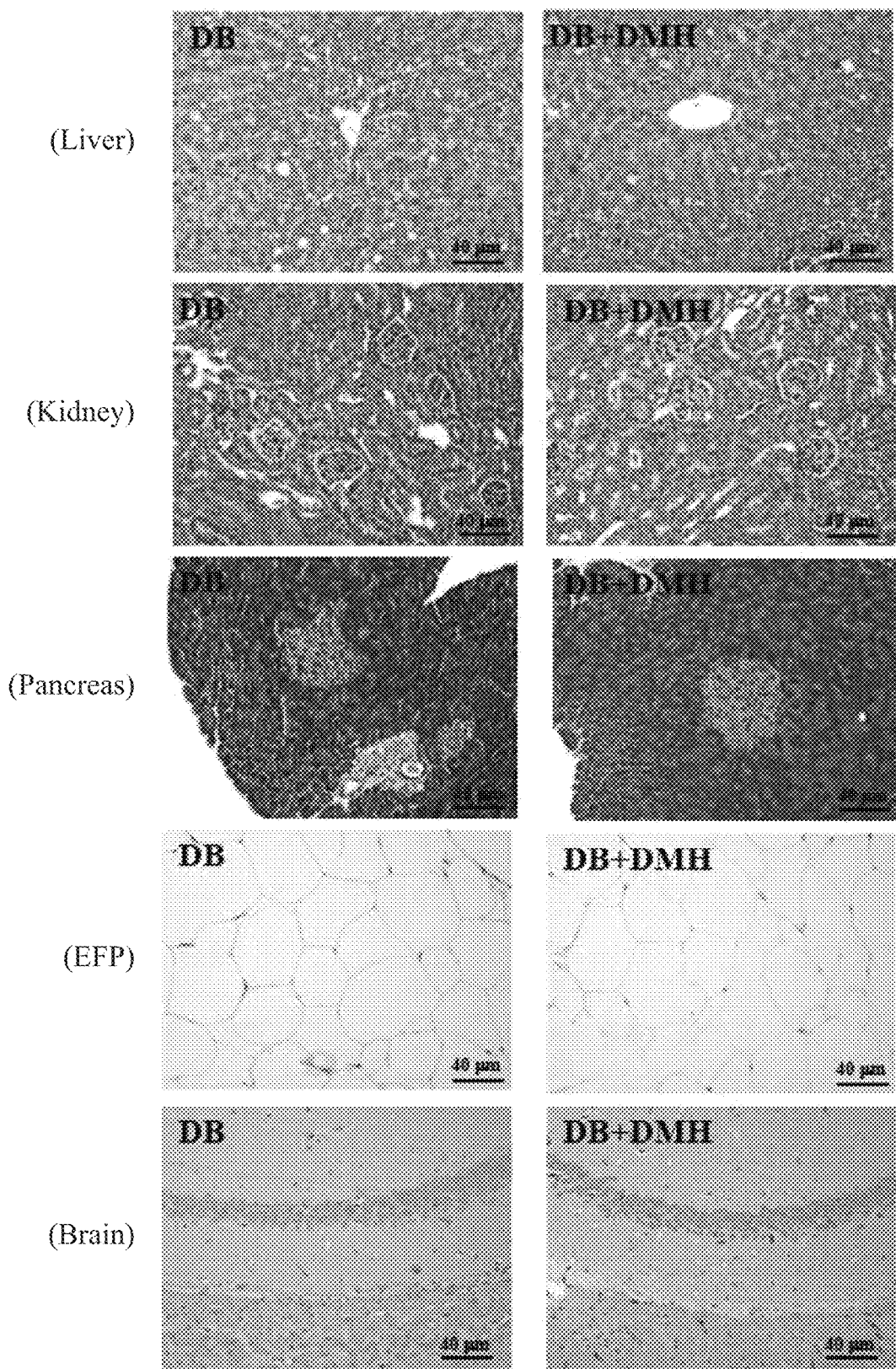
FIG. 2 shows the histology of different tissues after treatment of ertapenem. DB: db/db mice orally fed with distilled water and intraperitoneally injected (i.p.) with a saline solution. DB+DMH: db/db mice treated with ertapenem (0.41 mg/g bw/day), i.p. Scale bar: 40 μm. EFP: epididymal fat pads.

As shown in FIG. 2, results indicated no histological changes in the pancreases, the epididymal fat pads, and the brains of all mice.

Further, in liver tissues of the two groups, very slight to slight levels of glycogen storage were observed in the hepatocyte cytoplasm around the central venous region. The severity and incidence of such glycogen storage in the DB+DMH group is slighter than that in the DB group.

In kidney tissues, degeneration and necrosis of renal tubular epithelial cells, mineralization deposition, and hyaline cast were observed in some mice, while the severity and incidence of such histological changes were not significantly different between the two groups.

Overall, no significant injuries in brain, liver, kidney, pancreas, and epididymal fat pads were observed after ertapenem treatment.

Example 2: Effect of Ertapenem Treatment on a Glucose Metabolism Disorder after the Treatment has been Stopped To examine the effects of ertapenem and metformin (Met) treatments after the treatment has been stopped, eight 8-week-old m/m mice were used as the normal control (G1), and forty 8-week-old db/db mice were randomly divided into 5 groups (G2 to G6). Each group receives different treatments as explained in Table 5 below.

TABLE 5

Mice were divided into 6 groups for different treatments

| Group | Mice Used | Treatment |
|---|---|---|
| G1 | 8 m/m mice | Saline, i.p. (10 µL/g bw/day) |
| G2 | 8 db/db mice | Saline, i.p. (10 µL/g bw/day) |
| G3 | 8 db/db mice | Metformin, oral (0.3 mg/g bw/day) |
| G4 | 8 db/db mice | Ertapenem, i.p. (0.1 mg/g bw/day) |
| G5 | 8 db/db mice | Ertapenem, i.p. (0.2 mg/g bw/day) |
| G6 | 8 db/db mice | Ertapenem, i.p. (0.4 mg/g bw/day) |

Figure 3:
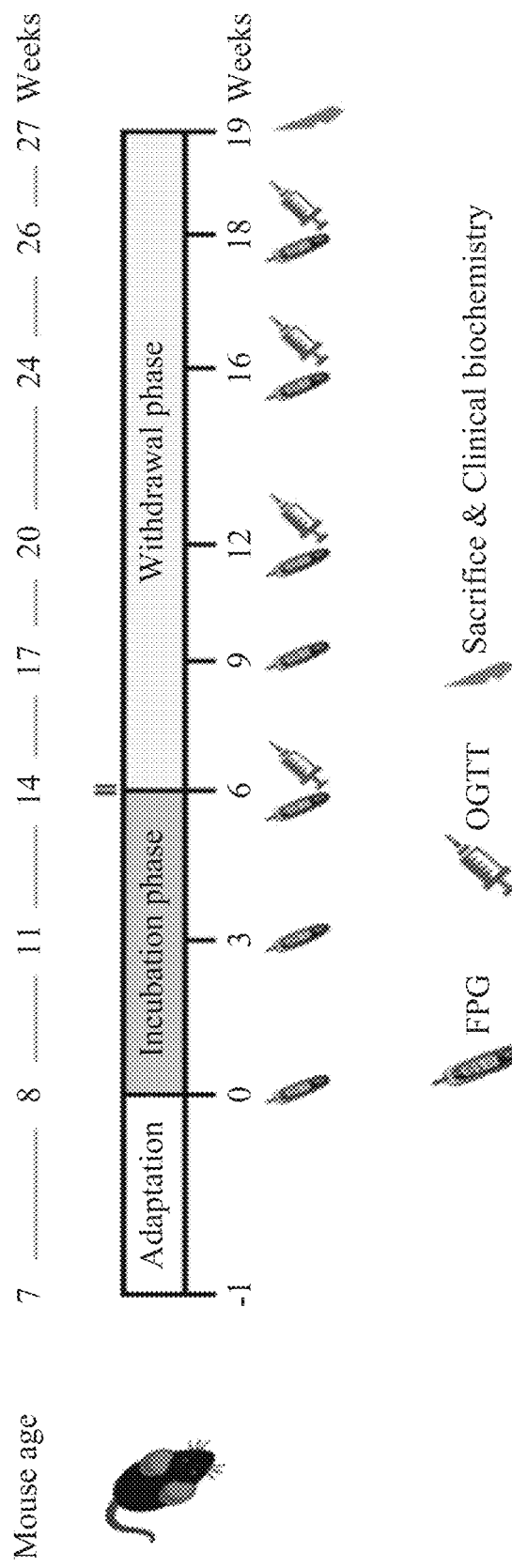
FIG. 3 illustrates the scheme of the treatment time, mouse ages and data acquisition time. Fasting plasma glucose (FPG) is measured at the weeks indicated with OneTouch UltraEasy. Oral glucose tolerance test (OGTT) was done at the weeks indicated with syringes. The levels of some inflammatory markers of liver and kidney were assayed at week 19 (indicated with an arrow). All medications were stopped at week 6.

The treatments lasted for a total of six weeks and all medications were stopped after six weeks. The tests were carried out at the time points with corresponding mouse age as illustrated in the scheme in FIG. 3. The tests and results were described as follows.

(2-1) Ertapenem Treatments Lowered Body Weight

As shown in Table 6 below, it was found that G1 mice had the lowest body weight during the entire study period (P<0.05). No significant changes in body weight were found among metformin treated mice (G3) and other testing mouse groups.

However, G4 mice had significant lower body weight than G2 and G3 mice during weeks 2 to 9, and G6 mice had lower body weight than G2 mice (at weeks 3 to 7 and 9) and G3 mice (during weeks 3 to 9). These data showed that ertapenem treatments (0.1 mg/g bw and 0.4 mg/g bw) had positive effects of body weight lowering in db/db mice. This effect occurred because db/db mice reduced their food and water intake under ertapenem treatment.

TABLE 6

Body weight among mouse groups

| # | Week | | | | | | |
|---|---|---|---|---|---|---|---|
| Groups | Baseline | 1 | 2 | 3 | 4 | 5 | 6 |
| G1: m/m mice | 19.26 ± 0.21$^a$ | 19.17 ± 0.16$^a$ | 20.33 ± 0.21$^a$ | 20.63 ± 0.25$^a$ | 20.84 ± 0.26$^a$ | 20.98 ± 0.27$^a$ | 21.04 ± 0.23$^a$ |
| G2: db/db mice | 31.16 ± 0.55$^b$ | 31.15 ± 0.61$^b$ | 33.61 ± 0.51$^c$ | 36.79 ± 0.56$^d$ | 37.59 ± 0.86$^c$ | 39.88 ± 1.05$^c$ | 40.85 ± 1.35$^{cd}$ |
| G3: db/db mice + 0.3 Met | 31.17 ± 0.47$^b$ | 30.81 ± 0.48$^b$ | 32.61 ± 0.46$^{bc}$ | 35.97 ± 0.57$^{cd}$ | 37.47 ± 0.79$^c$ | 40.15 ± 0.93$^c$ | 41.82 ± 0.98$^d$ |

TABLE 6-continued

Body weight among mouse groups

| | | | | | | | |
|---|---|---|---|---|---|---|---|
| G4: db/db mice + 0.1 DMH | 29.44 ± 2.09$^b$ | 29.21 ± 2.01$^b$ | 29.95 ± 1.79$^b$ | 32.38 ± 1.38$^b$ | 33.49 ± 1.13$^b$ | 35.72 ± 1.01$^b$ | 36.73 ± 0.95$^b$ |
| G5: db/db mice + 0.2 DMH | 31.70 ± 1.46$^b$ | 31.31 ± 1.48$^b$ | 31.81 ± 1.12$^{bc}$ | 34.36 ± 0.75$^{bc}$ | 35.55 ± 0.61$^{bc}$ | 37.76 ± 0.49$^{bc}$ | 39.06 ± 0.54$^{bc}$ |
| G6: db/db mice + 0.4 DMH | 31.61 ± 1.03$^b$ | 31.23 ± 0.98$^b$ | 31.62 ± 0.77$^{bc}$ | 33.98 ± 0.54$^b$ | 34.29 ± 0.59$^b$ | 36.44 ± 0.71$^b$ | 37.16 ± 0.8$^b$ |

| # | Week | | | | | | |
|---|---|---|---|---|---|---|---|
| Groups | 7 | 8 | 9 | 10 | 11 | 12 | 13 |
| G1: m/m mice | 20.76 ± 0.33$^a$ | 22.15 ± 0.39$^a$ | 22.56 ± 0.35$^a$ | 23.21 ± 0.31$^a$ | 23.89 ± 0.23$^a$ | 24.26 ± 0.23$^a$ | 24.43 ± 0.31$^a$ |
| G2: db/db mice | 40.10 ± 1.52$^{cd}$ | 41.00 ± 1.75$^{bc}$ | 42.09 ± 2.07$^{cd}$ | 42.23 ± 2.19$^b$ | 43.09 ± 2.5$^b$ | 43.76 ± 2.86$^b$ | 44.22 ± 3.14$^b$ |
| G3: db/db mice + 0.3 Met | 42.38 ± 1.25$^d$ | 43.04 ± 1.54$^c$ | 43.68 ± 1.58$^d$ | 43.40 ± 1.4$^b$ | 44.15 ± 1.37$^b$ | 45.24 ± 1.37$^b$ | 44.68 ± 1.6$^b$ |
| G4: db/db mice + 0.1 DMH | 36.68 ± 0.83$^b$ | 37.83 ± 0.77$^b$ | 38.46 ± 0.8$^b$ | 39.43 ± 0.81$^b$ | 40.86 ± 0.82$^b$ | 42.59 ± 0.87$^b$ | 44.21 ± 0.99$^b$ |
| G5: db/db mice + 0.2 DMH | 39.07 ± 0.45$^{bc}$ | 39.99 ± 0.39$^{bc}$ | 40.63 ± 0.27$^{bcd}$ | 41.39 ± 0.29$^b$ | 42.98 ± 0.35$^b$ | 44.66 ± 0.38$^b$ | 46.52 ± 0.45$^b$ |
| G6: db/db mice + 0.4 DMH | 37.16 ± 0.93$^b$ | 38.67 ± 1.24$^b$ | 39.72 ± 1.36$^{bc}$ | 40.81 ± 1.34$^b$ | 42.61 ± 1.31$^b$ | 44.54 ± 1.63$^b$ | 45.69 ± 1.86$^b$ |

| # | Week | | | | | |
|---|---|---|---|---|---|---|
| Groups | 14 | 15 | 16 | 17 | 18 | 19 |
| G1: m/m mice | 23.07 ± 0.3$^a$ | 24.41 ± 0.34$^a$ | 24.54 ± 0.33$^a$ | 24.59 ± 0.38$^a$ | 24.71 ± 0.41$^a$ | 23.58 ± 0.37$^a$ |
| G2: db/db mice | 43.10 ± 3.17$^b$ | 45.06 ± 3.23$^b$ | 46.08 ± 3.33$^b$ | 45.86 ± 3.36$^b$ | 46.57 ± 3.65$^b$ | 47.89 ± 3.7$^b$ |
| G3: db/db mice + 0.3 DMH | 43.94 ± 1.54$^b$ | 46.46 ± 1.39$^b$ | 47.68 ± 1.32$^b$ | 48.31 ± 1.38$^b$ | 49.57 ± 1.47$^b$ | 51.98 ± 1.66$^b$ |
| G4: db/db mice + 0.1 DMH | 43.56 ± 1.08$^b$ | 45.90 ± 1.18$^b$ | 46.80 ± 1.29$^b$ | 47.21 ± 1.26$^b$ | 48.14 ± 1.23$^b$ | 50.91 ± 1.22$^b$ |
| G5: db/db mice + 0.2 DMH | 46.10 ± 0.51$^b$ | 48.58 ± 0.55$^b$ | 49.65 ± 0.63$^b$ | 49.96 ± 0.68$^b$ | 50.71 ± 0.87$^b$ | 52.73 ± 1.04$^b$ |
| G6: db/db mice + 0.4 DMH | 45.08 ± 1.89$^b$ | 47.29 ± 1.95$^b$ | 48.79 ± 1.95$^b$ | 48.99 ± 1.87$^b$ | 50.70 ± 1.87$^b$ | 53.56 ± 1.99$^b$ |

In Table 6, values of group mean±SEM of body weight were represented and the difference in value was significant (P<0.05) between different italicized letters. For example, when comparing values represented by a with b, there existed statistical significance (P<0.05) in body weight between the two; and when comparing values represented by b with c, there existed statistical significance (P<0.05) in body weight between the two as well. In addition, value represented by be was significantly different from values represented by "a" or "d."

(2-2) Ertapenem Treatments Lowered Blood Glucose Level

FPG measurement was performed at mouse age 8, 11, 14, 17, 20, 24, and 26 weeks, in which FPG levels of 8 weeks old mice were set as the levels at week 0. Thus, FPG levels of 11, 14, 17, 20, 24, and 26 weeks old mice were the levels at 3, 6, 9, 12, 16, and 18 weeks, respectively, after treatment. The FPG levels of each group of mice were reported in Table 7 below

TABLE 7

Average FPG levels of mice

| # | Week | | | | | | |
|---|---|---|---|---|---|---|---|
| Groups | 0 | 3 | 6 | 9 | 12 | 16 | 18 |
| G1: m/m mice | 55 ± 3$^a$ | 61 ± 2$^a$ | 59 ± 4$^a$ | 76 ± 3$^a$ | 74 ± 6$^a$ | 89 ± 8$^a$ | 91 ± 4$^a$ |
| G2: db/db mice | 169 ± 27$^b$ | 209 ± 34$^c$ | 331 ± 40$^c$ | 286 ± 31$^{cd}$ | 374 ± 58$^d$ | 221 ± 59$^b$ | 377 ± 67$^b$ |
| G3: db/db mice + 0.3 Met | 160 ± 21$^b$ | 136 ± 13$^b$ | 222 ± 30$^b$ | 310 ± 25$^d$ | 267 ± 43$^{cd}$ | 215 ± 27$^b$ | 346 ± 50$^b$ |
| G4: db/db mice + 0.1 DMH | 139 ± 21$^b$ | 134 ± 21$^b$ | 219 ± 36$^b$ | 217 ± 37$^{bc}$ | 154 ± 30$^{ab}$ | 126 ± 43$^{ab}$ | 263 ± 58$^b$ |
| G5: db/db mice + 0.2 DMH | 142 ± 20$^b$ | 158 ± 25$^{bc}$ | 166 ± 21$^b$ | 212 ± 30$^{bc}$ | 191 ± 42$^{bc}$ | 154 ± 56$^{ab}$ | 308 ± 51$^b$ |
| G6: db/db mice + 0.4 DMH | 141 ± 23$^b$ | 121 ± 23$^{ab}$ | 175 ± 30$^b$ | 172 ± 27$^b$ | 166 ± 26$^{ac}$ | 108 ± 22$^{ab}$ | 266 ± 35$^b$ |

In Table 7, values of group means±SEM of FPG levels were shown, and the difference between the values was significant (P<0.05), as explained above.

As shown in Table 7 above, G1 mice had the lowest FPG levels at all measurement points (P<0.05).

At week 3, FPG levels of G3, G4, and G6 mice were significantly lower than those of G2 mice (P<0.05), suggesting that ertapenem treatments (0.1 mg/g bw and 0.4 mg/g bw) were as effective as metformin (0.3 mg/g bw) in lowering blood glucose levels in db/db mice.

At week 6, FPG levels of G3, G4, G5, and G6 mice were all significantly lower than those of G2 mice (P<0.05), indicating that ertapenem at all concentrations had a similar effect as metformin (0.3 mg/g bw) on blood glucose levels in the spontaneous type 2 diabetes db/db mice.

At weeks 9, 12, 16, and 18, FPG levels of metformin-treated mice (G3) were similar to those of untreated db/db mice (G2). This is conceivable as metformin has a plasma half-life of only approximately 6 hours and is cleared from blood within 24 hours.

Surprisingly, at week 9, the FPG levels of G6 mice were significantly lower than those of G2 (P<0.05) and G3 (P=0.0059) mice, and those of G4 and G5 mice were also lower than those of G3 mice (P<0.05). At week 12, FPG levels of G4, G5, and G6 mice were still lower than those of G2 mice, and there were no significant differences in FPG levels among G4, G5, and G6 mice. These results clearly showed that the effect of ertapenem is long-acting and long lasting.

These results clearly showed that ertapenem was as effective as metformin in controlling blood glucose levels, and that the blood-glucose-lowering effect of ertapenem lasted for at least 6 weeks in mice even though the treatment of ertapenem was stopped.

(2-3) Ertapenem Treatments Increased Oral Glucose Tolerance

OGTT was performed at 6, 12, 16, and 18 weeks after treatment (mouse age 14, 20, 24, and 26 weeks).

Figure 4:
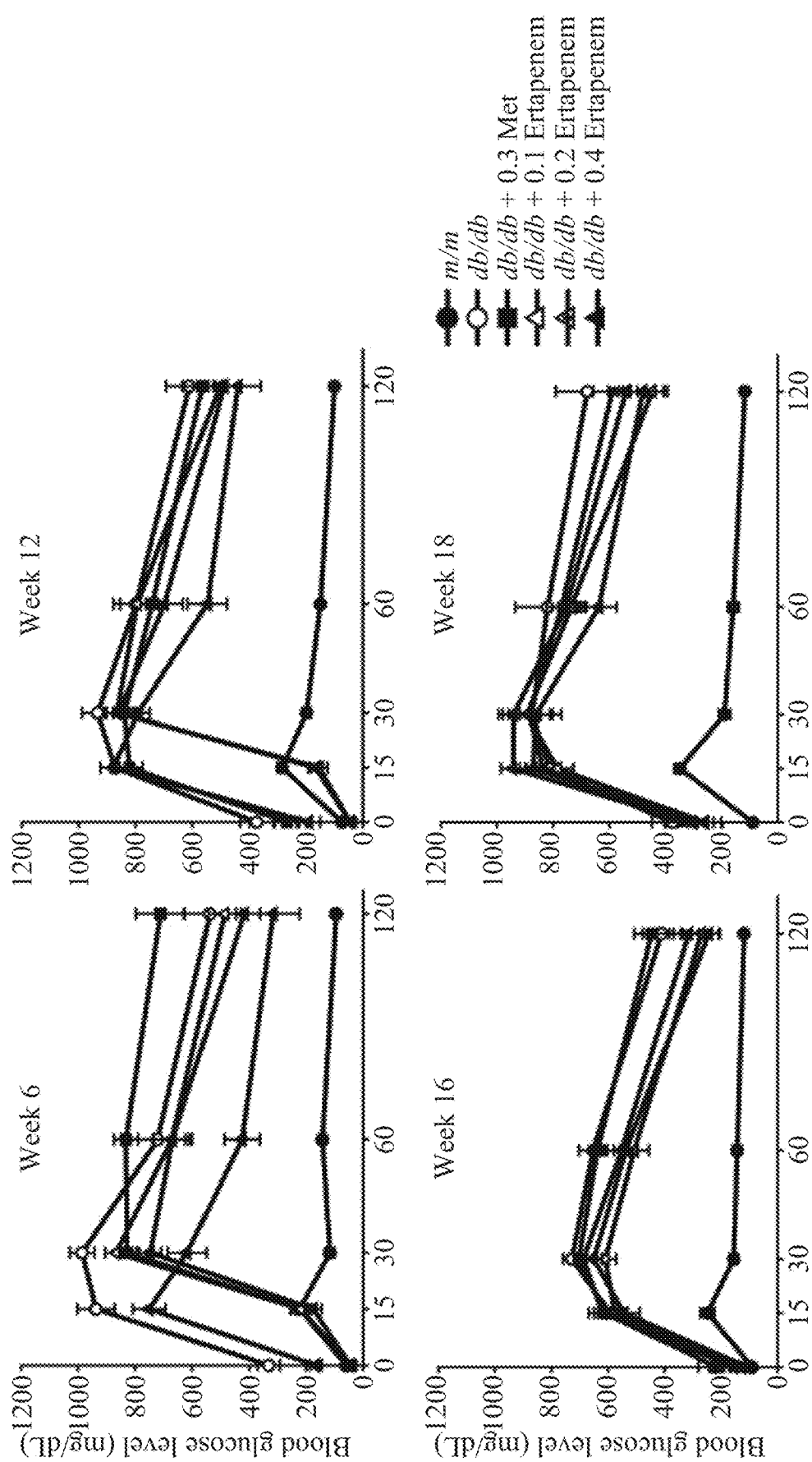
FIG. 4 shows the blood glucose concentrations at weeks 6, 12, 16, and 18 after treatment. ◆: m/m mice orally fed with distilled water and intraperitoneally injected (i.p.) with a saline solution. ◇: db/db mice treated the same as m/m mice. ■: db/db mice orally administrated with metformin (MET) (0.3 mg/g bw/day). □: db/db mice treated with ertapenem (0.1 mg/g bw/day), i.p. ▲: db/db mice treated with ertapenem (0.2 mg/g bw/day), i.p. △: db/db mice treated with ertapenem (0.4 mg/g bw/day), i.p.

As shown in Table 8 and FIG. 4, ertapenem significantly increased oral glucose tolerance (OGT) of db/db mice at most time points at weeks 6 and 12. However, no significant changes in OGT were found in metformin-treated mice at most measurement points, and only slight changes were observed among the groups of db/db mice at most measurement points in weeks 16 and 18.

TABLE 8

Levels of OGTT among groups at weeks 6, 12, 16, and 18

| # Groups | Time (min) | | | | |
|---|---|---|---|---|---|
| | 0 | 15 | 30 | 60 | 120 |
| Week 6 | | | | | |
| G1: m/m mice | $59 \pm 4^a$ | $223 \pm 28^a$ | $116 \pm 16^a$ | $143 \pm 10^a$ | $94 \pm 5^a$ |
| G2: db/db mice | $331 \pm 40^c$ | $937 \pm 66^c$ | $986 \pm 43^d$ | $721 \pm 98^d$ | $538 \pm 91^d$ |
| G3: db/db mice + 0.3 Met | $222 \pm 30^b$ | $828 \pm 33^{bc}$ | $832 \pm 42^c$ | $710 \pm 86^{cd}$ | $417 \pm 42^{cd}$ |
| G4: db/db mice + 0.1 DMH | $219 \pm 36^b$ | $866 \pm 38^{bc}$ | $671 \pm 62^b$ | $486 \pm 57^b$ | $286 \pm 44^{bc}$ |
| G5: db/db mice + 0.2 DMH | $166 \pm 21^b$ | $750 \pm 57^b$ | $618 \pm 68^b$ | $425 \pm 63^b$ | $316 \pm 92^{bc}$ |
| G6: db/db mice + 0.4 DMH | $175 \pm 30^b$ | $747 \pm 38^b$ | $669 \pm 69^b$ | $418 \pm 56^b$ | $223 \pm 27^{ab}$ |
| Week 12 | | | | | |
| G1: m/m mice | $74 \pm 6^a$ | $285 \pm 16^a$ | $198 \pm 14^a$ | $150 \pm 10^a$ | $99 \pm 7^a$ |
| G2: db/db mice | $374 \pm 58^d$ | $872 \pm 15^b$ | $933 \pm 55^d$ | $798 \pm 79^c$ | $610 \pm 82^c$ |
| G3: db/db mice | $267 \pm 43^{cd}$ | $821 \pm 47^b$ | $839 \pm 40^{cd}$ | $741 \pm 51^c$ | $564 \pm 70^c$ |
| G4: db/db mice | $154 \pm 30^{ab}$ | $866 \pm 36^b$ | $794 \pm 60^{bc}$ | $503 \pm 67^b$ | $372 \pm 83^b$ |
| G5: db/db mice | $191 \pm 42^{bc}$ | $879 \pm 45^b$ | $790 \pm 40^{bc}$ | $548 \pm 69^b$ | $440 \pm 81^{bc}$ |
| G6: db/db mice | $166 \pm 26^{ac}$ | $859 \pm 50^b$ | $698 \pm 65^b$ | $489 \pm 55^b$ | $324 \pm 47^b$ |
| Week 16 | | | | | |
| G1: m/m mice | $89 \pm 8^a$ | $248 \pm 24^a$ | $155 \pm 16^a$ | $143 \pm 15^a$ | $118 \pm 10^a$ |
| G2: db/db mice | $221 \pm 59^b$ | $592 \pm 58^b$ | $727 \pm 32^b$ | $652 \pm 50^b$ | $409 \pm 66^{cd}$ |
| G3: db/db mice | $215 \pm 27^b$ | $611 \pm 24^b$ | $703 \pm 15^b$ | $637 \pm 27^b$ | $444 \pm 62^{cd}$ |
| G4: db/db mice | $126 \pm 43^{ab}$ | $575 \pm 44^b$ | $609 \pm 39^c$ | $506 \pm 52^c$ | $270 \pm 65^{bd}$ |
| G5: db/db mice | $154 \pm 56^{ab}$ | $619 \pm 48^b$ | $686 \pm 34^{bc}$ | $551 \pm 52^{bc}$ | $314 \pm 54^{bc}$ |
| G6: db/db mice | $108 \pm 22^{ab}$ | $543 \pm 57^b$ | $650 \pm 29^{bc}$ | $535 \pm 43^{bc}$ | $244 \pm 35^{ab}$ |

TABLE 8-continued

Levels of OGTT among groups at weeks 6, 12, 16, and 18

| # | Time (min) | | | | |
|---|---|---|---|---|---|
| Groups | 0 | 15 | 30 | 60 | 120 |
| | Week 18 | | | | |
| G1: m/m mice | 91 ± 4$^a$ | 352 ± 19$^a$ | 193 ± 21$^a$ | 162 ± 19$^a$ | 120 ± 10$^a$ |
| G2: db/db mice | 377 ± 71$^b$ | 812 ± 84$^b$ | 875 ± 105$^b$ | 819 ± 115$^b$ | 679 ± 113$^c$ |
| G3: db/db mice | 346 ± 58$^b$ | 836 ± 58$^b$ | 885 ± 73$^b$ | 769 ± 55$^b$ | 589 ± 67$^{bc}$ |
| G4: db/db mice | 263 ± 58$^b$ | 785 ± 57$^b$ | 894 ± 49$^b$ | 735 ± 47$^b$ | 447 ± 53$^b$ |
| G5: db/db mice | 308 ± 51$^b$ | 943 ± 43$^b$ | 941 ± 53$^b$ | 753 ± 70$^b$ | 541 ± 63$^{bc}$ |
| G6: db/db mice | 266 ± 35$^b$ | 872 ± 46$^b$ | 860 ± 58$^b$ | 637 ± 64$^b$ | 480 ± 73$^b$ |

In Table 8, values of group means±SEM of OGTT levels were listed. The difference between the values was significant (P<0.05) if the italicized letters in superscript did not overlap, as explained above.

Then, the total area under the curve (AUC) in OGTT was plotted and calculated as shown in Table 9 below. Results showed that the AUCs of ertapenem-treated mice (G4 and G5) were significantly smaller (P<0.05) than those of metformin-treated mice (G3) and untreated db/db mice (G2) at weeks 6, 12, and 16. There was no statistical significances in AUCs between G2 and G3 groups at any measurement points.

TABLE 9

OGTT AUCs of six mouse groups

| # | Week | | | |
|---|---|---|---|---|
| Groups | 6 | 12 | 16 | 18 |
| G1: m/m mice | 260 ± 13$^a$ | 317 ± 12$^a$ | 297 ± 28$^a$ | 354 ± 29$^a$ |
| G2: db/db mice | 1455 ± 132$^c$ | 1518 ± 120$^d$ | 1142 ± 101$^c$ | 1532 ± 186$^b$ |
| G3: db/db mice + 0.3 Met | 1288 ± 93$^c$ | 1391 ± 94$^{cd}$ | 1143 ± 55$^c$ | 1456 ± 85$^b$ |
| G4: db/db mice + 0.1 DMH | 1033 ± 87$^b$ | 1096 ± 119$^b$ | 902 ± 85$^b$ | 1339 ± 80$^b$ |
| G5: db/db mice + 0.2 DMH | 916 ± 110$^b$ | 1171 ± 117$^{bc}$ | 1002 ± 88$^{bc}$ | 1462 ± 104$^b$ |
| G6: db/db mice + 0.4 DMH | 884 ± 84$^b$ | 1026 ± 94$^b$ | 916 ± 68$^b$ | 1291 ± 118$^b$ |

In Table 9 above, values of group means±SEM of OGTT AUCs were listed and the difference between the values was significant (P<0.05) if the italicized letters in superscript did not overlap, as explained above.

These results demonstrated that ertapenem effectively increased the oral glucose tolerance of db/db mice even after the treatment had been stopped for 10 weeks.

(2-4) Levels of Inflammatory Markers with DMH Treatment

The levels of the inflammation markers were measured at week 19. Blood glucose (GLU) and creatinine (Cr) were similar among mice in the test groups (G2 to G6), but were higher than those of G1. No significant changes of other inflammatory makers were found among mice in the test groups (G2 to G6).

(2-5) Histological change after DMH treatment

Liver, kidney, pancreas, and epididymal fat pad of the mice were examined histologically for injuries.

Figure 5:
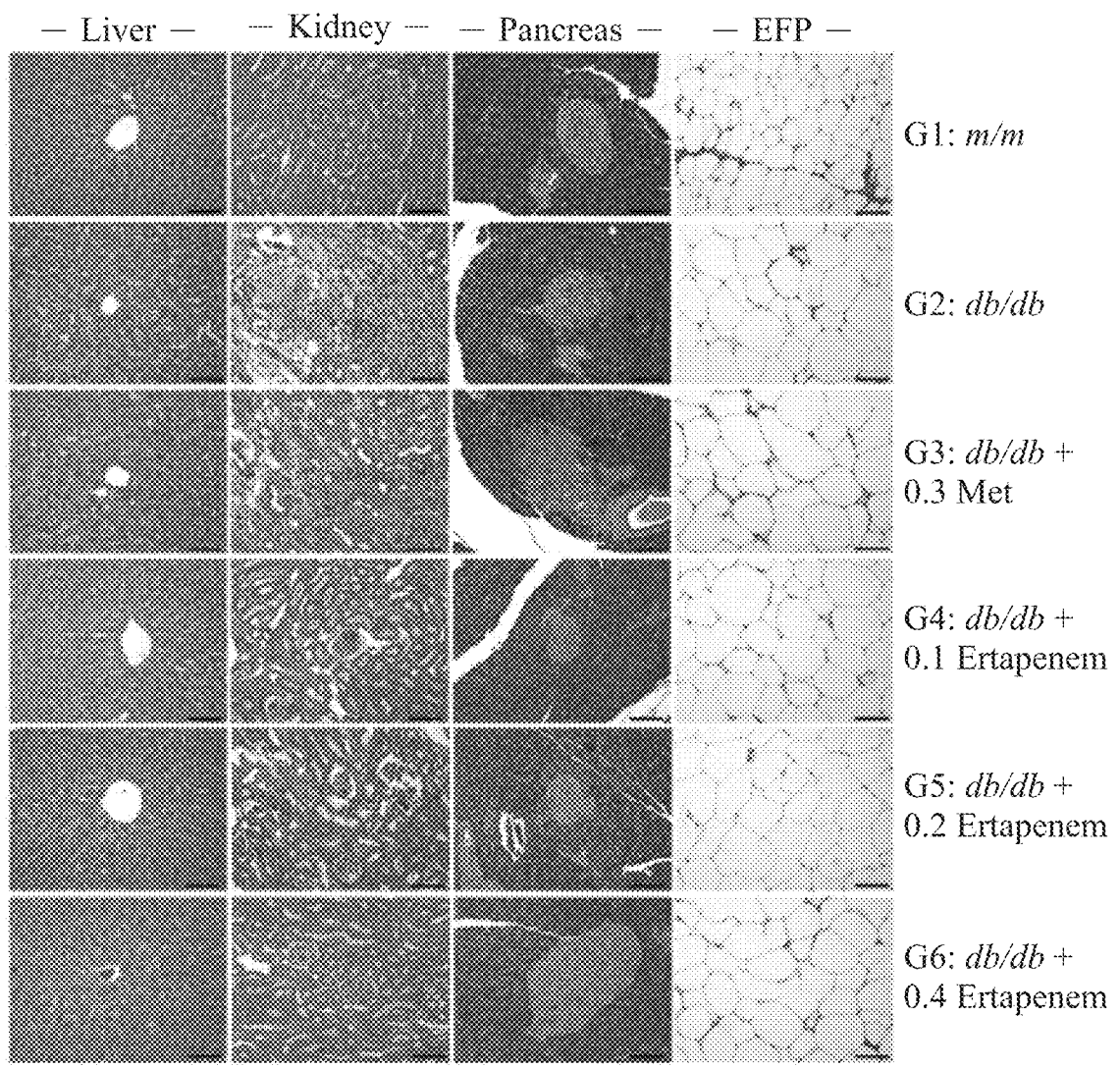
FIG. 5 shows the histology of four different tissues after treatment. G1: m/m mice, water ad libitum, saline, i.p. (10 μL/g bw) daily; G2: db/db mice, water ad libitum, saline, i.p. (10 μL/g bw) daily; G3: db/db mice, metformin (MET) orally (0.3 mg/g bw/day); G4: db/db mice, ertapenem, i.p. (0.1 mg/g bw/day); G5: db/db mice, ertapenem, i.p. (0.2 mg/g bw/day); G6: db/db mice, ertapenem, i.p. (0.4 mg/g bw/day). Scale bar: 40 μm. EFP: epididymal fat pads.

As shown in FIG. 5, results indicated no histological changes in the pancreases of all mice. A trace amount of glycogen was found accumulated in the hepatocytes surrounding the central vein in db/db mice, but not in m/m mice.

No histological changes were found in the kidneys of m/m mice, but degeneration and necrosis of renal tubular epithelial cells, mineralization deposition, and hyaline cast were observed in some db/db mice. These histological changes were more apparent in metformin-treated mice than in ertapenem-treated mice.

In epididymal fat pads, oil droplets were bigger in db/db mice than in m/m mice, and no histological differences among the groups were observed.

No significant injuries in liver, kidney, pancreas, and epididymal fat pads were observed after ertapenem treatment.

Example 3: Effect of Beta-Lactam Compound Treatment on a Glucose Metabolism Disorder after the Treatment has been Stopped To examine the effects of beta-lactam compounds after the treatment has been stopped, six 8-week-old m/m mice were used as the normal control (G7), and forty-two 7- or 8-week-old db/db mice were randomly divided into 7 groups (G8 to G14). Each group receives different treatments as explained in Table 10 below.

TABLE 10

Mice were divided into 8 groups for different treatments

| Group | Mice Used | Treatment |
|---|---|---|
| G7 | 6 m/m mice | Saline, i.p. (10 μL/g bw/day) |
| G8 | 6 db/db mice | Saline, i.p. (10 μL/g bw/day) |
| G9 | 6 db/db mice | Ertapenem, i.p. (0.41 mg/g bw/day) |
| G10 | 6 db/db mice | Meropenem hydrate, i.p. (0.205 mg/g bw/day) |
| G11 | 6 db/db mice | Ceftriaxone, i.p. (0.82 mg/g bw/day) |
| G12 | 6 db/db mice | Penicillin G, i.p. (1.473 mg/g bw/day) |
| G13 | 6 db/db mice | Tienam, i.p. (0.41 mg/g bw/day) |
| G14 | 6 db/db mice | Metformin, oral (0.3 mg/g bw/day) |

Specifically, the treatments received for each group are as followed:

G7: m/m mice, water ad libitum, saline i.p. (10 μL/g bw) daily;

G8: db/db mice, water ad libitum, saline i.p. (10 μL/g bw) daily;

G9: db/db mice, ertapenem (DMH) i.p. (0.41 mg/g bw, equivalent to 0.033 g/kg in human) daily;

G10: db/db mice, meropenem hydrate (MER) i.p. (0.205 mg/g bw, equivalent to 0.017 g/kg in human) daily;

G11: db/db mice, ceftriaxone (CEFT) i.p. (0.82 mg/g bw, equivalent to 0.067 g/kg in human) daily;

G12: db/db mice, penicillin G (PEN) i.p. (1.473 mg/g bw, equivalent to 0.12 g/kg in human) daily;

G13: db/db mice, tienam (TIE) i.p. (0.41 mg/g bw, equivalent to 0.033 g/kg in human) daily; and G14: db/db mice, metformin (MET) oral (0.3 mg/g bw) daily.

The treatments lasted for a total of three weeks; that is to say, all medications were stopped after three weeks. The tests or measurements were carried out at predestined time points, including the start of medication (also annotated as baseline or 0 week), the time point that the medication has been performed for 3 weeks (also annotated as week 3), the time point that the medication has been stopped for 3 weeks (also annotated as week 6), and the time point that the medication has been stopped for 6 weeks (also annotated as week 9). The tests and results were described as follows.

(3-1) Effect of Beta-Lactam Compound Treatments on Body Weight

As shown in Table 11 below, it was found that, except for the control group, G12 mice had the lowest body weight during the entire study period (P<0.05).

In Table 11 above, values of group mean±SEM of body weight were represented, and the difference between the values was significant (P<0.05) if the italicized letters in superscript did not overlap, as explained above.

(3-2) Effect of Beta-Lactam Compound Treatments on Food and Water Intake

As shown in Table 12 below, it was found that the DMH, CEFT, and PEN treatments significantly reduced the food intake in db/db mice (P<0.05), and the DMH, CEFT, TIE, and PEN treatments significantly reduced the water intake in db/db mice (P<0.05).

TABLE 12

Average food and water intake among mouse groups

| Groups | Diet intake (g/mice/day) | Water intake (mL/mice/day) |
|---|---|---|
| G7: m/m | 4.9 ± 1$^b$ | 4.4 ± 1$^a$ |
| G8: db/db | 6.0 ± 1$^c$ | 14.7 ± 1$^e$ |
| G9: db/db + DMH | 5.2 ± 1$^b$ | 8.4 ± 1$^c$ |
| G10: db/db + MER | 5.9 ± 1$^c$ | 14.7 ± 1$^e$ |
| G11: db/db + CEFT | 5.0 ± 1$^b$ | 7.1 ± 1$^b$ |
| G12: db/db + PEN | 4.0 ± 0.9$^a$ | 8.3 ± 4$^c$ |
| G13: db/db + TIE | 6.8 ± 1$^d$ | 9.4 ± 1$^c$ |
| G14: db/db + MET | 6.2 ± 1$^c$ | 12.1 ± 1$^d$ |

In Table 12 above, values of group mean±SEM of food and water intake were represented, and the difference between the values was significant (P<0.05) if the italicized letters in superscript did not overlap, as explained above.

(3-3) Effect of Beta-Lactam Compound Treatments on Oral Glucose Tolerance

OGTT was performed at week 6 and week 9, i.e., the time points that the medication has been stopped for 3 weeks and 6 weeks, respectively.

Figure 6A:
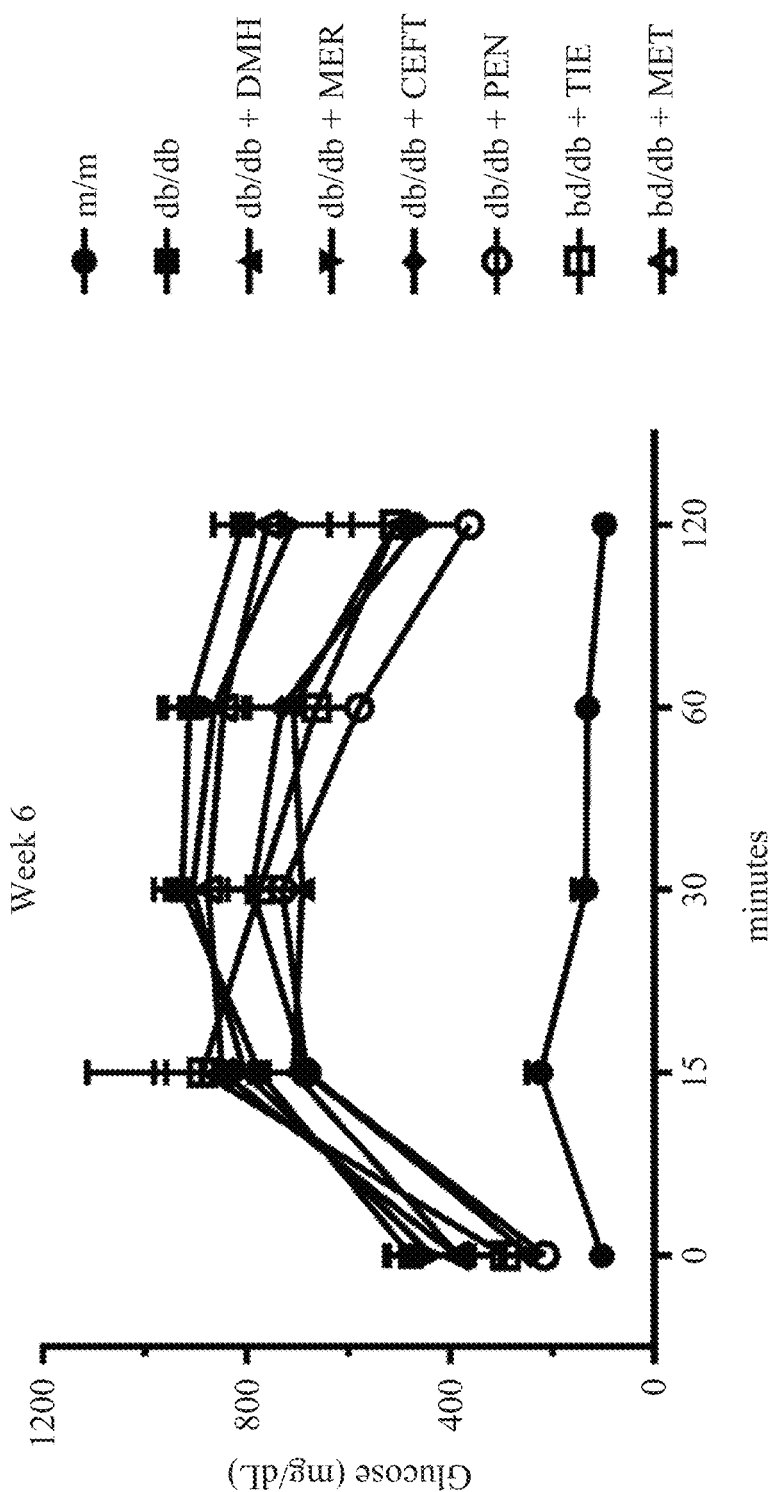
FIGS. 6A and 6B show the blood glucose concentrations at week 6 (FIG. 6A) and week 9 (FIG. 6B) after treatment. ◆: m/m mice orally fed with distilled water and intraperitoneally injected (i.p.) with a saline solution. ■: db/db mice treated the same as m/m mice. ▲: db/db mice treated with ertapenem (DMH) (0.41 mg/g bw/day), i.p. ✳: db/db mice treated with meropenem hydrate (MER) (0.205 mg/g bw/day), i.p. ●: db/db mice treated with ceftriaxone (CEFT) (0.82 mg/g bw/day), i.p. ✳: db/db mice treated with penicillin G (PEN) (1.473 mg/g bw/day). ⊟: db/db mice treated with tienam (TIE) (0.41 mg/g bw/day). ✳: db/db mice orally administrated with metformin (MET) (0.3 mg/g bw/day).
Figure 6B:
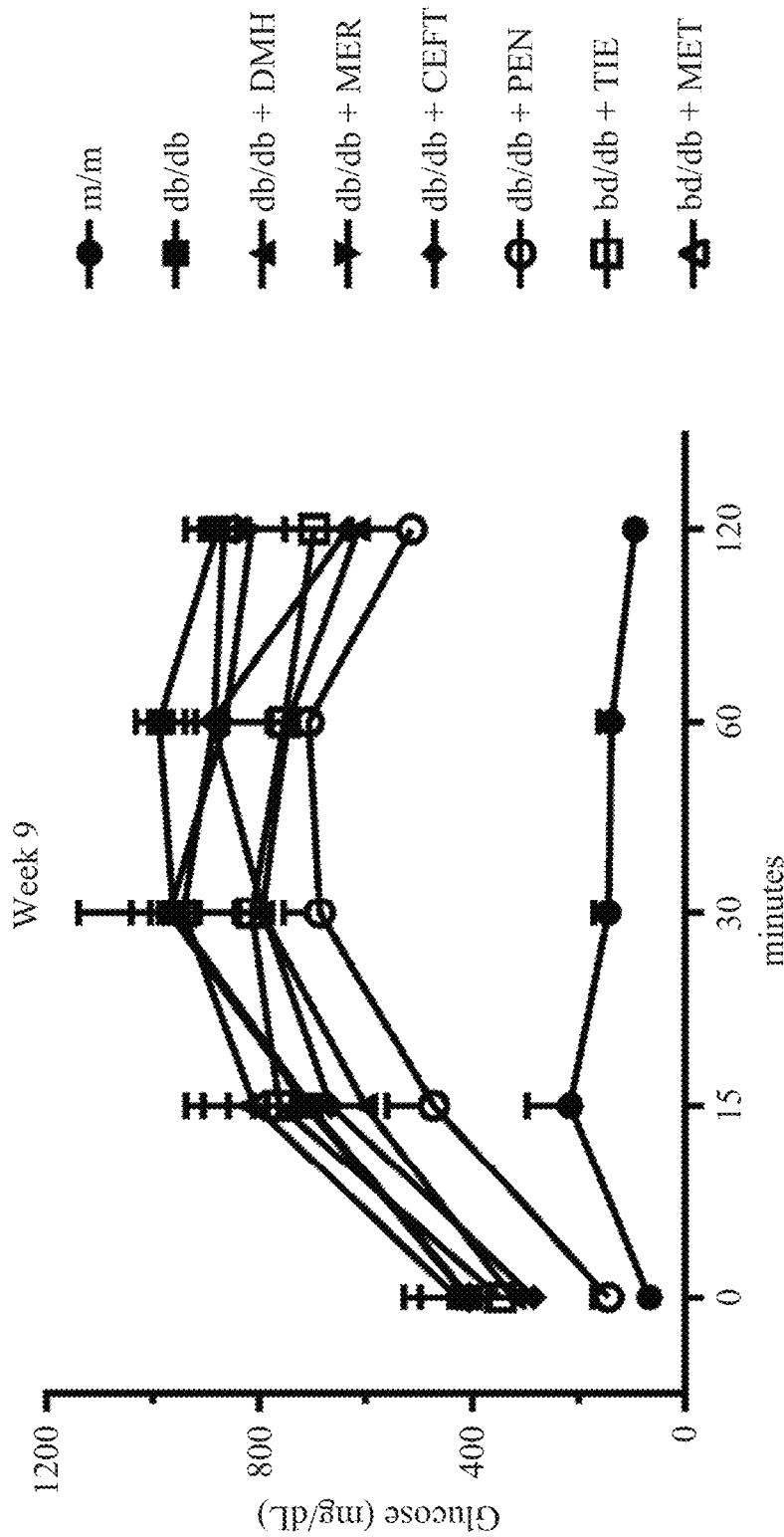

As shown in FIG. 6A, the glucose concentrations in the G9 and G12 groups were significantly lower than that in the G8 group at the time points of 30 min and 60 min; also, as shown in FIG. 6B, the glucose concentrations in the G9 and G12 groups were significantly lower than that in the G8 group at time points of 30 min, 60 min, and 120 min, suggesting that DMH and PEN are still effective in regulation of blood glucose homeostasis even though the medications had been stopped for at least 3 weeks.

Further, the total AUC in OGTT was plotted and calculated as shown in Table 13 below. Results showed that the AUCs of beta-lactam compound treatments (i.e., G9 to G13

TABLE 11

Body weight among mouse groups

| | | | Groups | | | | | |
|---|---|---|---|---|---|---|---|---|
| Week | G7 m/m | G8 db/db | G9 db/db + DMH | G10 db/db + MER | G11 db/db + CEFT | G12 db/db + PEN | G13 db/db + TIE | G14 db/db + MET |
| Baseline | 19.1 ± 1$^a$ | 29.6 ± 1$^b$ | 29.3 ± 1$^b$ | 28.3 ± 1$^b$ | 30.0 ± 1$^b$ | 31.1 ± 1$^b$ | 30.6 ± 2$^b$ | 28.9 ± 1$^b$ |
| Week 3 | 20.6 ± 1$^a$ | 34.6 ± 1$^{cd}$ | 33.5 ± 1$^{cd}$ | 33.6 ± 1$^{cd}$ | 32.9 ± 1$^{cd}$ | 25.7 ± 1$^b$ | 31.9 ± 2$^c$ | 35.9 ± 1$^d$ |
| Week 6 | 22.2 ± 1$^a$ | 37.7 ± 1$^{bc}$ | 35.1 ± 1$^b$ | 37.1 ± 1b$^c$ | 34.1 ± 2$^b$ | 24.6 ± 1$^a$ | 37.7 ± 2$^{bc}$ | 39.5 ± 1$^c$ |
| Week 9 | 23.5 ± 1$^a$ | 39.5 ± 1$^c$ | 40.0 ± 1$^c$ | 38.2 ± 2$^c$ | 38.8 ± 2$^c$ | 32.4 ± 1$^b$ | 42.6 ± 3$^c$ | 39.7 ± 1$^c$ |
| Final | 22.9 ± 1$^a$ | 37.6 ± 1$^c$ | 38.3 ± 1$^c$ | 36.0 ± 2$^{bc}$ | 37.8 ± 2$^c$ | 32.2 ± 1$^b$ | 40.6 ± 3$^c$ | 37.0 ± 1$^c$ | group) were smaller (P<0.05) than that of untreated mice (G8 group) even after the treatments had been stopped for at least 3 weeks.

TABLE 13

OGTT AUCs of eight mouse groups

| Groups | Week 6 | Week 9 |
|---|---|---|
| G7: m/m | 267 ± 9$^a$ | 267 ± 13$^a$ |
| G8: db/db | 1691 ± 33$^c$ | 1769 ± 30$^f$ |
| G9: db/db + DMH | 1263 ± 135$^b$ | 1356 ± 149$^{bc}$ |
| G10: db/db + MER | 1599 ± 39$^c$ | 1648 ± 61$^{def}$ |
| G11: db/db + CEFT | 1276 ± 69$^b$ | 1483 ± 37$^{ce}$ |
| G12: db/db + PEN | 1088 ± 91$^b$ | 1181 ± 69$^b$ |
| G13: db/db + TIE | 1301 ± 109$^b$ | 1453 ± 101$^{cd}$ |
| G14: db/db + MET | 1603 ± 46$^c$ | 1707 ± 43$^f$ |

In Table 13 above, values of group mean±SEM of OGTT AUCs were listed, and the difference between the values was significant (P<0.05) if the italicized letters in superscript did not overlap, as explained above.

(3-4) Plasma Biochemical Parameter Analysis

The concentrations of AST, ALT, BUN, Cr and HbA1c in plasma of each group of mice were measured at week 9, i.e., after the treatments had been stopped for 6 weeks. The results were summarized in Table 14 below.

It was found that the levels of AST, ALT, BUN, Cr and HbA1c in the diabetes mice were reduced by treating with beta-lactam compounds. For example, DMH may reduce the levels of AST, ALT, and HbA1c; MER may reduce the level of AST; CEFT may reduce the levels of AST, ALT, BUN, Cr, and HbA1c; PEN may reduce the level of ALT, BUN, Cr and HbA1c; and TIE may reduce the level of HbA1c, even after the treatments had been stopped for 6 weeks.

In Table 14 above, values of group mean±SEM of each parameter were listed, and the difference between the values was significant (P<0.05) if the italicized letters in superscript did not overlap, as explained above.

From the above, it can be seen that the beta-lactam compounds of the present disclosure exhibit a long-acting effect in improving a glucose metabolism disorder, and thus can be useful for improving the quality of patients' lives and their compliance with the treatment of a glucose metabolism disorder.

While some of the embodiments of the present disclosure have been described in detail above, it is, however, possible for those of ordinary skill in the art to make various modifications and changes to the particular embodiments shown without substantially departing from the teaching and advantages of the present disclosure. Such modifications and changes are encompassed in the spirit and scope of the present disclosure as set forth in the appended claims.

What is claimed is:

1. A method for long-acting prevention or treatment of type 2 diabetes in a subject suffering from type 2 diabetes, comprising administering to the subject an effective amount of penicillin G,
wherein the long-acting prevention or treatment of type 2 diabetes is prevention or treatment of a symptom of type 2 diabetes for more than two days after administration penicillin G.

2. The method of claim 1, wherein the long-acting prevention or treatment lasts for at least one week after the administration.

3. The method of claim 1, wherein the long-acting prevention or treatment lasts for at least 6 weeks after the administration.

4. The method of claim 1, wherein the long-acting prevention or treatment lasts for 6 to 10 weeks after the administration.

* * * * *

TABLE 14

Plasma biochemical parameters in each group of mice

| Groups | Week | | | | |
|---|---|---|---|---|---|
| | AST (U/L) | ALT (U/L) | BUN (mg/dL) | Creatinine (mg/dL) | HbA1c (%) |
| G7: m/m | 80 ± 2$^a$ | 43 ± 4$^a$ | 17 ± 1$^a$ | 0.377 ± 0.01$^a$ | 3.8 ± 0.1$^a$ |
| G8: db/db | 130 ± 22$^{bcd}$ | 88 ± 8$^{bc}$ | 44 ± 3$^{cd}$ | 0.465 ± 0.01$^{bc}$ | 7.2 ± 0.2$^e$ |
| G9: db/db + DMH | 127 ± 13$^{ad}$ | 79 ± 8$^{bc}$ | 44 ± 2$^d$ | 0.467 ± 0.01$^{bd}$ | 5.8 ± 0.3$^d$ |
| G10: db/bd + MER | 93 ± 8$^{ab}$ | 89 ± 5$^{bcd}$ | 43 ± 2$^{bd}$ | 0.488 ± 0.03$^{cde}$ | 6.9 ± 0.3$^e$ |
| G11: db/db + CEFT | 104 ± 10$^{ac}$ | 80 ± 7$^{bc}$ | 38 ± 2$^{bc}$ | 0.428 ± 0.01$^b$ | 4.9 ± 0.2$^c$ |
| G12: db/db + PEN | 169 ± 24$^{de}$ | 72 ± 20$^{ab}$ | 41 ± 5$^{bd}$ | 0.424 ± 0.02$^{ab}$ | 4.2 ± 0.2$^a$ |
| G13: db/db + TIE | 212 ± 43$^e$ | 104 ± 10$^{cd}$ | 47 ± 4$^d$ | 0.473 ± 0.05$^{be}$ | 5.7 ± 0.2$^d$ |
| G14: db/db + MET | 194 ± 17$^e$ | 116 ± 12$^d$ | 37 ± 1$^b$ | 0.517 ± 0.01$^e$ | 6.7 ± 0.2$^e$ |